United States Patent
Yoganathan et al.

(10) Patent No.: US 8,568,473 B2
(45) Date of Patent: Oct. 29, 2013

(54) SYSTEMS AND METHODS FOR ENABLING HEART VALVE REPLACEMENT

(75) Inventors: Ajit P. Yoganathan, Tucker, GA (US); Jorge Hernan Jimenez, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 1045 days.

(21) Appl. No.: 12/097,173

(22) PCT Filed: Dec. 15, 2006

(86) PCT No.: PCT/US2006/062199
§ 371 (c)(1),
(2), (4) Date: Oct. 20, 2008

(87) PCT Pub. No.: WO2007/100410
PCT Pub. Date: Sep. 7, 2007

(65) Prior Publication Data
US 2009/0157174 A1    Jun. 18, 2009

Related U.S. Application Data

(60) Provisional application No. 60/750,558, filed on Dec. 15, 2005.

(51) Int. Cl.
*A61F 2/24*       (2006.01)
(52) U.S. Cl.
USPC ........................................................ 623/2.11
(58) Field of Classification Search
USPC .............. 623/1.24, 1.26, 2.1, 2.11, 2.17, 2.38
See application file for complete search history.

(56) References Cited

U.S. PATENT DOCUMENTS

| | | | |
|---|---|---|---|
| 3,656,185 A | | 4/1972 | Carpentier |
| 3,671,979 A | | 6/1972 | Moulopoulos |
| 3,769,983 A | * | 11/1973 | Merav ...................... 128/207.15 |
| 4,055,861 A | | 11/1977 | Carpentier et al. |
| 4,056,854 A | | 11/1977 | Boretos et al. |
| 4,164,046 A | | 8/1979 | Cooley |
| 4,217,665 A | | 8/1980 | Bex et al. |
| 4,275,469 A | | 6/1981 | Gabbay |
| 4,602,911 A | | 7/1986 | Ahmadi et al. |

(Continued)

FOREIGN PATENT DOCUMENTS

| EP | 0338994 | 10/1989 |
|---|---|---|
| EP | 0595791 | 5/1994 |

(Continued)

OTHER PUBLICATIONS

Examination Report for related European Patent Application No. 06850306.9 dated Apr. 8, 2011.

(Continued)

*Primary Examiner* — Gregory Anderson
(74) *Attorney, Agent, or Firm* — Benjamin C. Wiles, Esq.; Ryan A. Schneider, Esq.; Troutman Sanders LLP

(57) ABSTRACT

The present invention describes a cardiac prosthetic system (400) comprising: an anchoring conduit (200) having a harbor (415), the harbor including a first releasably engaging component (515); a temporary valve (305) and a heart valve prosthesis (420) having a second releasably engaging component (445) enabled to be securely coupled and uncoupled from the first releasably engaging component (515) of the harbor (415).

42 Claims, 10 Drawing Sheets

(56) References Cited

U.S. PATENT DOCUMENTS

| | | |
|---|---|---|
| 4,790,844 A | 12/1988 | Ovil |
| 4,917,097 A | 4/1990 | Proudian et al. |
| 4,993,428 A | 2/1991 | Arms |
| 5,010,892 A | 4/1991 | Colvin et al. |
| 5,041,130 A | 8/1991 | Cosgrove et al. |
| 5,061,277 A | 10/1991 | Carpentier et al. |
| 5,064,431 A | 11/1991 | Gilbertson et al. |
| 5,104,407 A | 4/1992 | Lam et al. |
| 5,201,880 A | 4/1993 | Wright et al. |
| 5,258,021 A | 11/1993 | Duran |
| 5,306,296 A | 4/1994 | Wright et al. |
| 5,316,016 A | 5/1994 | Adams et al. |
| 5,344,442 A | 9/1994 | Deac |
| 5,396,887 A | 3/1995 | Imran |
| 5,450,860 A | 9/1995 | O'Connor |
| 5,480,424 A | 1/1996 | Cox |
| 5,496,336 A | 3/1996 | Cosgrove et al. |
| 5,533,515 A | 7/1996 | Coller et al. |
| 5,573,007 A | 11/1996 | Bobo, Sr. |
| 5,593,435 A | 1/1997 | Carpentier et al. |
| 5,607,471 A | 3/1997 | Seguin et al. |
| 5,662,704 A | 9/1997 | Gross |
| 5,674,279 A | 10/1997 | Wright et al. |
| 5,728,064 A | 3/1998 | Burns et al. |
| 5,733,331 A | 3/1998 | Peredo |
| 5,752,522 A | 5/1998 | Murphy |
| 5,776,189 A | 7/1998 | Khalid |
| 5,814,098 A | 9/1998 | Hinnenkamp et al. |
| 5,824,066 A | 10/1998 | Gross |
| 5,824,069 A | 10/1998 | Lemole |
| 5,848,969 A | 12/1998 | Panescu et al. |
| 5,855,563 A | 1/1999 | Kaplan et al. |
| 5,865,801 A | 2/1999 | Houser |
| 5,888,240 A | 3/1999 | Carpentier et al. |
| 5,902,308 A | 5/1999 | Murphy |
| 5,919,147 A | 7/1999 | Jain |
| 5,921,934 A | 7/1999 | Teo |
| 5,921,935 A | 7/1999 | Hickey |
| 5,924,984 A | 7/1999 | Rao |
| 5,931,868 A | 8/1999 | Gross |
| 5,972,030 A | 10/1999 | Garrison et al. |
| 6,010,531 A | 1/2000 | Donlon et al. |
| 6,019,739 A | 2/2000 | Rhee et al. |
| 6,024,918 A | 2/2000 | Hendriks et al. |
| 6,066,160 A | 5/2000 | Colvin et al. |
| 6,081,737 A | 6/2000 | Shah |
| 6,083,179 A | 7/2000 | Oredsson |
| 6,099,475 A | 8/2000 | Seward et al. |
| 6,102,945 A | 8/2000 | Campbell |
| 6,110,200 A | 8/2000 | Hinnenkamp |
| 6,117,091 A | 9/2000 | Young et al. |
| 6,143,024 A | 11/2000 | Campbell et al. |
| 6,159,240 A | 12/2000 | Sparer et al. |
| 6,165,120 A | 12/2000 | Schweich, Jr. et al. |
| 6,183,512 B1 | 2/2001 | Howanec, Jr. et al. |
| 6,187,040 B1 | 2/2001 | Wright |
| 6,217,610 B1 | 4/2001 | Carpentier et al. |
| 6,231,602 B1 | 5/2001 | Carpentier et al. |
| 6,250,308 B1 | 6/2001 | Cox |
| 6,258,122 B1 | 7/2001 | Tweden et al. |
| 6,312,464 B1 | 11/2001 | Navia |
| 6,332,893 B1 | 12/2001 | Mortier et al. |
| 6,391,054 B2 | 5/2002 | Carpentier et al. |
| 6,406,420 B1 | 6/2002 | McCarthy et al. |
| 6,406,493 B1 | 6/2002 | Tu et al. |
| 6,409,759 B1 | 6/2002 | Peredo |
| 6,419,696 B1 | 7/2002 | Ortiz et al. |
| 6,602,288 B1 | 8/2003 | Cosgrove et al. |
| 6,602,289 B1 | 8/2003 | Colvin et al. |
| 6,619,291 B2 | 9/2003 | Hlavka et al. |
| 6,626,899 B2 | 9/2003 | Houser et al. |
| 6,629,534 B1 | 10/2003 | St. Goar et al. |
| 6,669,687 B1 | 12/2003 | Saadat |
| 6,709,456 B2 | 3/2004 | Langberg et al. |
| 6,718,985 B2 | 4/2004 | Hlavka et al. |
| 6,719,786 B2 | 4/2004 | Ryan et al. |
| 6,723,038 B1 | 4/2004 | Schroeder et al. |
| 6,726,715 B2 | 4/2004 | Sutherland |
| 6,726,717 B2 | 4/2004 | Alfieri et al. |
| 6,764,510 B2 | 7/2004 | Vidlund et al. |
| 6,790,230 B2 | 9/2004 | Beyersdorf et al. |
| 6,797,002 B2 | 9/2004 | Spence et al. |
| 6,800,090 B2 | 10/2004 | Alferness et al. |
| 6,802,860 B2 | 10/2004 | Cosgrove et al. |
| 6,805,710 B2 | 10/2004 | Bolling et al. |
| 6,805,711 B2 | 10/2004 | Quijano et al. |
| 6,830,586 B2 | 12/2004 | Quijano et al. |
| 6,858,039 B2 | 2/2005 | McCarthy |
| 6,896,690 B1 | 5/2005 | Lambrecht et al. |
| 6,908,482 B2 | 6/2005 | McCarthy et al. |
| 6,918,917 B1 | 7/2005 | Nguyen et al. |
| 6,921,407 B2 | 7/2005 | Nguyen et al. |
| 6,942,694 B2 | 9/2005 | Liddicoat et al. |
| 6,945,996 B2 | 9/2005 | Sedransk |
| 6,955,689 B2 | 10/2005 | Ryan et al. |
| 6,966,924 B2 | 11/2005 | Holmberg |
| 6,986,775 B2 | 1/2006 | Morales et al. |
| 6,991,649 B2 | 1/2006 | Sievers |
| 7,018,406 B2 | 3/2006 | Seguin et al. |
| 7,037,334 B1 | 5/2006 | Hlavka et al. |
| 7,066,954 B2 | 6/2006 | Ryan et al. |
| 7,101,395 B2 | 9/2006 | Tremulis et al. |
| 7,112,219 B2 | 9/2006 | Vidlund et al. |
| 7,118,595 B2 | 10/2006 | Ryan et al. |
| 7,125,421 B2 | 10/2006 | Tremulis et al. |
| 7,166,126 B2 | 1/2007 | Spence et al. |
| 7,166,127 B2 | 1/2007 | Spence et al. |
| 7,186,262 B2 | 3/2007 | Saadat |
| 7,247,134 B2 | 7/2007 | Vidlund et al. |
| 7,294,148 B2 | 11/2007 | McCarthy |
| 7,320,704 B2 * | 1/2008 | Lashinski et al. ............ 623/2.11 |
| 7,329,280 B2 | 2/2008 | Bolling et al. |
| 7,513,909 B2 * | 4/2009 | Lane et al. ..................... 623/2.4 |
| 7,527,647 B2 | 5/2009 | Spence |
| 8,025,695 B2 * | 9/2011 | Fogarty et al. ............... 623/2.38 |
| 2001/0034551 A1 | 10/2001 | Cox |
| 2002/0029080 A1 | 3/2002 | Mortier et al. |
| 2002/0129820 A1 | 9/2002 | Ryan et al. |
| 2002/0133180 A1 | 9/2002 | Ryan et al. |
| 2002/0169504 A1 | 11/2002 | Alferness et al. |
| 2002/0173844 A1 | 11/2002 | Alfieri et al. |
| 2003/0033009 A1 | 2/2003 | Gabbay |
| 2003/0040793 A1 | 2/2003 | Marquez |
| 2003/0055495 A1 | 3/2003 | Pease et al. |
| 2003/0078653 A1 | 4/2003 | Vesely et al. |
| 2003/0083742 A1 | 5/2003 | Spence et al. |
| 2003/0093148 A1 | 5/2003 | Bolling et al. |
| 2003/0105519 A1 | 6/2003 | Fasol et al. |
| 2004/0006384 A1 | 1/2004 | McCarthy |
| 2004/0088047 A1 | 5/2004 | Spence et al. |
| 2004/0122513 A1 | 6/2004 | Navia et al. |
| 2004/0133192 A1 | 7/2004 | Houser et al. |
| 2004/0186566 A1 | 9/2004 | Hindrichs et al. |
| 2004/0210301 A1 | 10/2004 | Obermiller |
| 2004/0249452 A1 | 12/2004 | Adams et al. |
| 2004/0249453 A1 | 12/2004 | Cartledge et al. |
| 2005/0004666 A1 | 1/2005 | Alfieri et al. |
| 2005/0043790 A1 | 2/2005 | Seguin |
| 2005/0043791 A1 | 2/2005 | McCarthy et al. |
| 2005/0070999 A1 | 3/2005 | Spence |
| 2005/0075719 A1 | 4/2005 | Berghiem |
| 2005/0075727 A1 | 4/2005 | Wheatley |
| 2005/0080402 A1 | 4/2005 | Santamore et al. |
| 2005/0131533 A1 | 6/2005 | Alfieri et al. |
| 2005/0137689 A1 | 6/2005 | Salahieh et al. |
| 2005/0143811 A1 | 6/2005 | Realyvasquez |
| 2005/0182487 A1 | 8/2005 | McCarthy et al. |
| 2005/0192666 A1 | 9/2005 | McCarthy |
| 2005/0197696 A1 | 9/2005 | Gomez Duran |
| 2005/0246014 A1 | 11/2005 | McCarthy |
| 2005/0256567 A1 | 11/2005 | Lim et al. |
| 2005/0256568 A1 | 11/2005 | Lim et al. |
| 2005/0256569 A1 | 11/2005 | Lim et al. |
| 2005/0261759 A1 | 11/2005 | Lambrecht et al. |

(56) References Cited

U.S. PATENT DOCUMENTS

| | | |
|---|---|---|
| 2005/0267572 A1 | 12/2005 | Schoon et al. |
| 2005/0278022 A1 | 12/2005 | Lim |
| 2005/0288776 A1 | 12/2005 | Shaoulian et al. |
| 2005/0288777 A1 | 12/2005 | Rhee et al. |
| 2005/0288778 A1 | 12/2005 | Shaoulian et al. |
| 2005/0288780 A1 | 12/2005 | Rhee et al. |
| 2005/0288782 A1 | 12/2005 | Moaddeb et al. |
| 2005/0288783 A1 | 12/2005 | Shaoulian et al. |
| 2006/0015178 A1 | 1/2006 | Moaddeb et al. |
| 2006/0015179 A1 | 1/2006 | Bulman-Fleming et al. |
| 2006/0020333 A1 | 1/2006 | Lashinski et al. |
| 2006/0020336 A1 | 1/2006 | Liddicoat |
| 2006/0025856 A1 | 2/2006 | Ryan et al. |
| 2006/0025858 A1 | 2/2006 | Alameddine |
| 2006/0030885 A1 | 2/2006 | Hyde |
| 2006/0052868 A1 | 3/2006 | Mortier et al. |
| 2006/0149368 A1 | 7/2006 | Spence |
| 2006/0167474 A1 | 7/2006 | Bloom et al. |
| 2006/0195012 A1 | 8/2006 | Mortier et al. |
| 2006/0195183 A1 | 8/2006 | Navia et al. |
| 2006/0229708 A1 | 10/2006 | Powell et al. |
| 2006/0241340 A1 | 10/2006 | Schroeder et al. |
| 2006/0259135 A1 | 11/2006 | Navia et al. |
| 2007/0038294 A1 | 2/2007 | Navia |
| 2007/0049952 A1 | 3/2007 | Weiss |
| 2007/0050020 A1 | 3/2007 | Spence |
| 2007/0066863 A1 | 3/2007 | Rafiee et al. |
| 2007/0100439 A1 | 5/2007 | Cangialosi et al. |
| 2007/0118151 A1 | 5/2007 | Davidson |
| 2007/0118154 A1 | 5/2007 | Crabtree |
| 2007/0123979 A1 | 5/2007 | Perier et al. |
| 2007/0129758 A1 | 6/2007 | Saadat |
| 2007/0162111 A1 | 7/2007 | Fukamachi et al. |
| 2007/0173930 A1 | 7/2007 | Sogard et al. |
| 2007/0208357 A1 | 9/2007 | Houser et al. |
| 2007/0213582 A1 | 9/2007 | Zollinger et al. |
| 2007/0255396 A1 | 11/2007 | Douk et al. |
| 2008/0027268 A1 | 1/2008 | Buckner et al. |
| 2008/0039935 A1 | 2/2008 | Buch et al. |
| 2008/0051807 A1 | 2/2008 | St. Goar et al. |
| 2008/0081942 A1 | 4/2008 | Pai et al. |
| 2009/0177278 A1 | 7/2009 | Spence |
| 2009/0192602 A1 | 7/2009 | Kuehn |
| 2009/0192603 A1 | 7/2009 | Ryan |
| 2009/0192604 A1 | 7/2009 | Gloss |
| 2009/0192605 A1 | 7/2009 | Gloss et al. |
| 2009/0192606 A1 | 7/2009 | Gloss et al. |

FOREIGN PATENT DOCUMENTS

| | | |
|---|---|---|
| EP | 0860151 | 8/1998 |
| EP | 1034753 | 9/2000 |
| FR | 2708458 | 8/1993 |
| JP | 2004089696 | 3/2004 |
| WO | 9119456 | 12/1991 |
| WO | 9503757 | 2/1995 |
| WO | 9640006 | 12/1996 |
| WO | 9741801 | 11/1997 |
| WO | 9742871 | 11/1997 |
| WO | 9806329 | 2/1998 |
| WO | 9911201 | 3/1999 |
| WO | WO 99/30647 | 6/1999 |
| WO | 9951169 | 10/1999 |
| WO | 9965423 | 12/1999 |
| WO | 0032105 | 6/2000 |
| WO | WO 00/47139 | 8/2000 |
| WO | 0119292 | 3/2001 |
| WO | 0126586 | 4/2001 |
| WO | 0147438 | 7/2001 |
| WO | 0187191 | 11/2001 |
| WO | 0203892 | 1/2002 |
| WO | 03020178 | 3/2003 |
| WO | 03041617 | 5/2003 |
| WO | 2004004607 | 1/2004 |
| WO | WO 2004/112658 | 12/2004 |
| WO | 2005004753 | 1/2005 |
| WO | 2005034813 | 4/2005 |
| WO | 2005082278 | 9/2005 |
| WO | 2005110290 | 11/2005 |
| WO | 2006041877 | 4/2006 |
| WO | 2006133186 | 12/2006 |
| WO | 2007050506 | 5/2007 |
| WO | 2007100408 | 9/2007 |
| WO | WO2007/100408 | 9/2007 |
| WO | WO2007/100409 | 9/2007 |
| WO | WO2007/100410 | 9/2007 |
| WO | 2007131513 | 11/2007 |
| WO | 2008058940 | 5/2008 |
| WO | 2008063537 | 5/2008 |
| WO | 2008094469 | 8/2008 |
| WO | 2008098226 | 8/2008 |

OTHER PUBLICATIONS

International Search Report and Written Opinion dated Oct. 12, 2007 for related PCT Application No. PCT/US2006/062185.

International Search Report and Written Opinion dated Sep. 27, 2007 for related PCT Application No. PCT/US2006/062192.

International Search Report and Written Opinion dated Oct. 31, 2007 for related PCT Application No. PCT/US2006/062199.

Adams, David, et al., "Large Annuloplasty Rings Facilitate Mitral Valve Repair in Barlow's Disease", The Society of Thoracic Surgeons, vol. 82, pp. 2096-2101, 2006.

Alonso-Lei, F. et al., "Adjustable Annuloplasty for Tricuspid Insufficiency" The Annals of Thoracic Surgery, vol. 46, No. 3, pp. 368-369, Sep. 1988.

Bolling, Steven F. et al., "Mitral Valve Reconstruction in the Patient with Heart Failure", Heart Failure Reviews, vol. 6, pp. 177-185, 2001.

Bolling, Steven F. et al., "Surgical Alternatives for Heart Failure", The Journal of Heart and Lung Transplantation, vol. 20, No. 7, pp. 729-733, 2001.

Carpentier, Alain F. et al., "The "Physio-Ring": An Advanced Concept in Mitral Valve Annuloplasty", The Thirty-First Annual Meeting of the Society of Thoracic Surgeons, pp. 1177-1186, Jan. 30-Feb. 2, 1995.

"Carpentier-Edwards Classic Annuloplasty Ring With Duraflo Treatment Models 4425 and 4525 for Mitral and Tricuspid Valvuloplasty", Baxter Healthcare Corporation, pp. 1-6, 1998.

"Carpentier-Edwards Physio Annuloplasty Ring", Edwards Lifesciences LLC, pp. 1-2, 2003.

Cochran, Richard P. et al., "Effect of Papillary Muscle Position on Mitral Valve Function: Relationship to Homografts", The Society of Thoracic Surgeons, vol. 66, pp. S155-S161, 1998.

Flachskampf, Frank A. et al., "Analysis of Shape and Motion of the Mitral Annulus in Subjects With and Without Cardiomyopathy by Echocardiographic 3-Dimensional Reconstruction", The Journal of the American Society of Echocardiography, vol. 13, pp. 277-287, 2000.

Gatti, Giuseppe et al., "Preliminary Experience in Mitral Valve Repair Using the Cosgrove-Edwards Annuloplasty Ring", Interactive Cardiovascular and Thoracic Surgery, vol. 2, No. 3, pp. 256-261, 2003, http://icvts.ctsnetjournals.org/cgi/content/full/2/3/256.

Melo, J.Q. et al., "Atrioventricular Valve Repair Using Externally Adjustable Flexible Rings", The Journal of Thoracic and Cardiovascular Surgery, vol. 110, No. 5, pp. 1333-1337, Nov. 1995.

"MGH Study Shows Mitral Valve Prolapse Not a Stroke Risk Factor", Massachusetts General Hospital, pp. 1-3, Jun. 1999, http://www.mgh.harvard.edu/DEPTS/pubaffairs/releases/Jun_99_mitral_valve.htm.

Miller, Craig D., "Ischemic Mitral Regurgitation Redux—To Repair or to Replace?", The Journal of Thoracic and Cardiovascular Surgery, vol. 22, No. 6, pp. 1059-1062, Dec. 2001.

Salgo, Ivan S. et al., "Effect of Annular Shape on Leaflet Curvature in Reducing Mitral Leaflet Stress", Journal of the American Heart Association, Circulation 2002, vol. 106, pp. 711-717, Jul. 22, 2002, http://circ.ahajournals.org/cgi/reprint/106/6/711.

(56) References Cited

OTHER PUBLICATIONS

Seguin, J.R. et al., "Advance in Mitral Valve Repair Using a Device Flexible in Three Dimensions", The St. Jude Medical-Seguin Annuloplasty Ring, The American Society for Artificial Internal Organs Journal, vol. 42, No. 6, pp. M368-M371, 1996.

Smolens, Iva A. et al., "Mitral Valve Repair in Heart Failure", The European Journal of Heart Failure, vol. 2, pp. 365-371, 2000.

"Techniques for 3D Quantitative Echocardiography", University of Washington Cardiovascular Research & Training Center Cardiac Imaging Research Lab, pp. 1-4, http://depts.washington.edu/cvrtc/apples.html, 2010.

Watanabe, Nozomi, et al., "Mitral Annulus Flattens in Ischemic Mitral Regurgitation: Geometric Differences Between Inferior and Anterior Myocardial Infarction: A Real-Time 3-Dimensional Echocardiographic Study" Journal of the American Heart Association, Circulation 2005, vol. 112, pp. 458-468, Aug. 30, 2005, http://circ.ahajournals.org/cgi/content/full/112/9_suppl/I-458.

Examination Report issued by the Canadian Patent Office dated May 15, 2013 for related CA application No. 2,668,988.

* cited by examiner

SYSTEMS AND METHODS FOR ENABLING HEART VALVE REPLACEMENT

BENEFIT AND PRIORITY CLAIMS

This application is a 35 U.S.C. §371 U.S. National Stage of International Application No. PCT/US2006/062199 filed 15 Dec. 2006, which claims priority to and the benefit of U.S. Ser. No. 60/750,558, filed 15 Dec. 2005. All of said prior applications are hereby incorporated by reference in their entireties as if fully set forth below.

CROSS REFERENCE TO RELATED APPLICATIONS

This application claims the benefit of U.S. Provisional Application No. 60/750,558, filed 15 Dec. 2005, which is hereby incorporated by reference in its entirety as if fully set forth below.

FIELD OF THE INVENTION

This invention refers generally to the field of heart valve replacement, and specifically to the implants tools and methods for preparing a native heart valve for a prosthesis and for providing a replaceable heart valve prosthesis.

BACKGROUND OF THE INVENTION

Cardiovascular disease accounts for nearly fifty percent of deaths in both the developed world and in developing countries. Indeed, the risk of dying from heart disease is greater than the risk from AIDS and all forms of cancer combined. Cardiovascular disease causes 12 million deaths in the world each year. It is the leading cause of death in the U.S., killing some 950,000 people each year. It also accounts for a significant amount of disability and diminished quality of life. Some 60 million people in the U.S. alone have some form of heart disease. Therefore, a great need exists for the advancement of devices and procedures to cure, treat, and correct a wide variety of forms of heart disease.

Normal heart function primarily relies upon the proper function of each of the four valves of the heart, which pass blood through the four chambers of the heart. The four chambers of the heart include the right atrium and left atrium, the upper chambers, and the right ventricle and left ventricle, the lower chambers. The four valves, controlling blood flow in the chambers, include the tricuspid, mitral, pulmonary, and aortic valves. Heart valves are complex structures that rely on the interaction of many components to open and close the valve. More particularly, each of the four valves of the heart have leaflets, comprised of fibrous tissue, which attach to the walls of the heart and aid in controlling the flow of blood through the valve. The mitral valve has two leaflets and the tricuspid valve has three leaflets. The aortic and pulmonary valves have three leaflets that are more aptly termed "cusps," stemming from their half moon shape.

The cardiac cycle involves the pumping and distribution of both oxygenated and deoxygenated blood within the four chambers. In systole, or the rhythmic contraction of the heart cycle, blood that has been oxygenated by the lungs enters the heart into the left atrium. During diastole, or the resting phase of heart cycle, the left atrial pressure exceeds the left ventricle pressure; thus, oxygenated blood flows through the mitral valve, a one way inflow valve, into the left ventricle. The contraction of the left ventricle in systole pumps the oxygenated blood through the aortic valve, into the aorta, and is passed to the body. When the left ventricle contracts in systole, the mitral valve closes and the oxygenated blood passes into the aorta rather than back through the mitral valve. On the other side of the heart, deoxygenated blood returns from the body and enters the heart through the right atrium. This deoxygenated blood flows through the tricuspid valve into the right ventricle. When the right ventricle contracts, the tricuspid valve closes and the deoxygenated blood is pumped through the pulmonary valve. Deoxygenated blood is directed to the pulmonary vascular bed for oxygenation, and the cardiac cycle repeats itself.

The performance of the cardiac cycle by the various components of the heart is a complex and intricate process. Deficiency in one of the components of the heart or deficiency in the performance of the cardiac cycle most often leads to one or more of the numerous different types of heart disease. One prevalent heart disease condition is aortic valve regurgitation. Aortic valve regurgitation has many levels of severity. Aortic regurgitation is the diastolic flow of blood from the aorta into the left ventricle. Regurgitation is due to incompetence of the aortic valve or disturbance of the valvular apparatus (e.g., leaflets, annulus of the aorta) resulting in diastolic flow of blood into the left ventricular chamber. Incompetent closure of the aortic valve can result from intrinsic disease of the cusp, diseases of the aorta, or trauma. Aortic regurgitation may be a chronic disease process or it may occur acutely, presenting as heart failure. Diastolic reflux through the aortic valve can lead to left ventricular volume overload.

FIG. 1 provides an illustration of a normal aortic valve 101. The perspective of the aortic valve 101 shown in FIG. 1 provides a diagram of a dissected and flattened aortic valve 101 to best illustrate its components. The aortic valve 101 has three cusps or leaflets, the left coronary cusp 105, the right coronary cusp 110, and the non-coronary cusp 115. These three cusps control the flow of blood from the left ventricle into the aorta, which ultimately conveys oxygenated blood to the tissues of the body for their nutrition. Located just above the three cusps, 105, 110, and 115, are the sinuses of the valsalva 125 and each sinus corresponds to each individual cusp. The origins of the coronary arteries are proximate the sinuses of the valsalva 125. As shown in FIG. 1, the orifice 130 for the right coronary artery is located just above the right coronary leaflet cusp 110. Similarly, the orifice 135 for the left coronary artery is located just above the left coronary leaflet cusp 105. Additionally, the aortic valve 101 is juxtaposed with the anterior mitral annulus 120.

In a normal aortic valve 101, when the left ventricle contracts in systole, the aortic valve cusps, 105, 110, and 115, open into the aorta and blood flows from the left ventricle into the aorta. When the left ventricle rests in diastole, the cusps, 105, 110, and 115, meet and close, covering the area of the valve annulus. Therefore, the cusps, 105, 110, and 115, prevent regurgitation, or backflow of blood, into the left ventricle during diastole.

The aortic valve 101 is located in the aortic root of the aorta. The aortic root has two main components, the inner (aorto-ventricular junction) and the outer (sino-tubular junction), which are considered the functional aortic annulus. It is this aortic annulus that supports the fibrous structures of the cusps, 105, 110, and 115.

As shown in FIG. 1, the function of the aortic valve, involves the complex interaction of numerous components. If one of the components or functions of the complicated interaction fails, then aortic valve regurgitation can result. For example, a bicuspid valve, calcification of the cusps, or stenosis or restricted motion of the cusps can lead to aortic regurgitation. Prolonged and/or severe aortic valve regurgitation can lead to compensatory left ventricle dilation. Aortic valve regurgitation is a progressive condition that, if not corrected, can be fatal.

In addition to aortic regurgitation, pulmonic regurgitation is highly prevalent heart disease that causes or contributes to increasing numbers of heart disease each year. Like aortic regurgitation, pulmonic regurgitation involves the incompetence of the pulmonic valve and its failure to completely close. In a normal pulmonic valve, the right ventricle contracts in systole and pumps blood through the open pulmonic valve into the pulmonary artery. Contrastingly, when the right ventricle rests in diastole, the pulmonic valve closes and prevents the backflow of blood into the right ventricle. In cases of pulmonic regurgitation, the pulmonic valve fails to completely close and permits a regurgitant flow of blood from the pulmonary artery back into the right ventricle during diastole. This backflow of blood can overload the right ventricle and lead to right ventricle dilation.

There a large variety of methods available in the prior art to treat different types of valvular heart disease such as pulmonic regurgitation and aortic regurgitation. A highly popular and successful method of treatment of these conditions involves the use of prosthetic cardiac valves, such as mechanical valves and bioprosthetic valves.

The most commonly used replacement devices are mechanical and bioprosthetic valves, with homografts and autografts less commonly used. From 1990 to 2000, the breakdown of valve replacement percentages as indicated by the Society of Thoracic Surgery Registry for patients less than 60 years of age with aortic valve disease was a follows: mechanical valves in 77% of patients, bioprosthetic valves in 13%, homograft valves in 5%, and the Ross procedure in 5%.

A mechanical valve is a device constructed from man-made materials and is used to replace patients damaged or diseased native heart valves. More than 60 percent of heart valve replacements have been made with mechanical prostheses due to their durability and superior hemodynamics which offer minimal resistance to flow. Despite their superior durability, the turbulent fluid mechanics of mechanical valves causes damage to blood cells. This damage to the blood cells can include thrombus formation. The possible thrombus formation initiated by disturbed flow patterns necessitates life-long anticoagulant therapy. Further problems are associated with mechanical heart valves, including small stagnant regions proximate the hinges that sometimes lead to bacterial infections causing further heart damage.

Many different valve designs with different materials of construction have evolved to address the deficiencies of mechanical valves, such as to reduce thrombus formation and decrease the mechanical stresses that can cause blood cell damage. Several synthetic polymers have been tested as leaflet materials such as silicone, polyolefin rubbers and polytetrafluoroethylene. Laboratory fatigue testing has illustrated that polyurethane valves are capable of achieving more than 800 million cycles (~20 years of "normal" function). Valve leaflets constructed of a commercially available polyetherurethane when implanted in sheep showed superior valve function to that of bioprosthetic valves. Thus, polymeric valves could offer a clinical advantage with the promise of improved durability compared to bioprostheses and low thrombogenicity compared to mechanical valves. Although polymeric valves show great promise they have been under development for several decades and no design has made it to commercialization due to failure or calcification within its normal biological environment. As a result, mechanical valves are still the primary choice for surgical correction and have to be used in conjunction with anticoagulation therapies, which reduces the quality of life of the patient and exposes them to risks associated with bleeding.

Bioprosthetic valves are tissue valves made of animal tissue (i.e. xenografts) and are easily and readily available. These were introduced in the early 1970s as an attempt to avoid some of the disadvantages of mechanical valves. Flexible, trileaflet, biological tissue valves mimic their natural counterparts more closely than mechanical heart valves. Their central flow characteristics offer better hemodynamic efficiency, and their biological surfaces enhance thromboresistance as compared to mechanical prostheses.

The valves are chemically treated to make the tissue less immunogenic and thus less likely to incite an allergic or immunological reaction in the recipient. As a result, the tissue comprising the valve is non-viable, and therefore, subject to degeneration with time. Bioprosthetic valves are commonly employed in elderly patients for whom the risk of bleeding complications are high and in those whose desired way of life precludes the discipline of anticoagulation therapy.

The biological tissues are usually fixed with different chemicals (glutaraldehyde, Aminooleic acid, ethanol etc) and under different protocols in order to increase the durability of the valve. Leaflet fixation stiffens the tissue unintentionally, alters internal shear properties, increases shear stiffness, stress relaxation and hysteresis, and causes substantial dehydration, all of which lead to valve failure due to calcification or tissue tearing. Although some chemical treatments are effective in reducing calcification, they do not prevent disruption of collagen fibers. Collagen fibers exposed to blood flow are damaged and cannot be repaired due to lack of viable cells within the leaflet. Therefore because of tissue degradation and calcification bioprosthetic valves have a limited durability which may average around 10 years. Although bioprosthetic valve technology has advanced, their limited durability is a problem which may take a long time to address completely.

Currently a new generation of bioprosthetic valves and mechanical valves is being developed, and these valves may be implanted percutaneously. While these bioprosthetic and mechanical valves present a number of improvements over the prior art, the safety and success of these devices is significantly reduced by the complexity of their deployment.

Many devices exist in the prior art, which attempt to address the complexity of properly deploying a bioprosthetic valve. For example, U.S. Pat. No. 6,790,230 to Beyersdorf et al. ("'230 patent") discloses a conventional valve anchoring element, which has non-cylindrical form that corresponds to the shape of the aorta. The anchoring element of the '230 patent is provided such that a replacement valve can be sutured to the interior of the anchoring element. The anchoring element and associated replacement valve can then be delivered via a catheter to the aorta and expanded such as to disable the native aortic valve. Thereby, the expansion of the anchoring element in the aorta serves to disable the native aortic valve and, at the same time, enable the replacement valve.

U.S. Pat. No. 7,018,406 to Seguin et al. ("'406 patent) discloses a prosthetic valve assembly to be used in replacing a deficient native valve. The prosthesis described in the '406 patent includes a tissue valve supported on a self expandable stent. The prosthesis is capable of percutaneous delivery to the native valve, at which the prosthesis can be expanded and attached to the lumen wall. The '406 patent describes that the typical valve is made biological materials and is attached to the valve support band with a suture. The valve attached to the valve support band is collapsible along its center axis so that the entire structure can be compressed and loaded onto a catheter for delivery.

U.S. Patent Publication No. 2005/0137689 to Salahieh et al. ("'689 Publication") discloses a method for endovascularly replacing a heart valve. The method disclosed in the '689 Publication includes the steps of delivering a replacement valve and an expandable anchor in an unexpanded configuration within a catheter to a vicinity of a heart valve. Once delivered to the proper location, the anchor is deployed from the catheter and expanded to contact tissue at an anchor site. The expansion of the anchor simultaneously deploys the collapsed replacement heart valve contained within the anchor.

The deployment of these conventional bioprosthetic valves requires the precise execution of a number of steps and techniques, and inaccurate execution of even one of these steps can lead to a patient fatality. For example, proper deployment of the bioprosthetic valve can require expansion of the valve anchor at a precise location within the native heart valve. Furthermore, the valve anchor must properly engage the lumen wall when expanded such that a good surface of contact is made with the lumen wall to enable a tight contact. Good and safe seating of the valve anchor is critical, as it must withstand blood flow under high pressure, high velocity, and a significant amount of pulsation. Furthermore, a replacement valve positioned in an inadequately anchored valve will not be able to resist the forces of the constantly changing vessel wall diameter and turbulent blood flow. Improper and insufficient deployment can lead to migration of the valve anchor before or after the deployment of the bioprosthetic valve. Even the slightest migration of the valve anchor can have many detrimental results, including covering the openings to an arterial outlet or compromising the function of the replacement valve.

Not only is precise placement of the valve anchor of a bioprosthetic valve important, a secure seating of the valve anchor is critical because improper or insufficient deployment of the valve anchor can lead to leakage between the anchor and the lumen wall. It is often the case that a deficient native valve and areas of tissue around the native valve have irregularities and calcification that are a result of, or are contributing factors to, the heart disease at issue. The typical calcification, thickening, and hardening of the cardiac annulus can make it increasingly difficult to achieve proper sealing quality for the valve anchor of the bioprosthetic valve. For example, heavy calcification on the native valve can lead to bumpy and even surfaces, which can translate to a low quality seal of the valve anchor with the lumen wall if not deployed properly. Not only can calcification make it difficult to properly seat the valve anchor, fragments of the calcified deposits can be loosened during the seating of the valve anchor and thus enter blood stream causing damage and possible blockage.

While many of the conventional devices have attempted to address the issues and complexities associated with the minimally invasive deployment of a heart valve replacement, significant problems and risks for the patient still exist. A large majority of the risk is due to the nature of the deployment of the replacement valves. Often, a surgeon has one shot to correctly deploy the heart valve prosthesis. Furthermore, the endovascular deployment of the heart valve provides a surgeon with a limited ability to verify the correctness and accuracy of the deployment. The surgeon's deployment of the replacement valve is often visually aided only by a two dimensional ultrasound image. This two dimensional image leaves a large amount of room for error in the three dimensional deployment of the replacement valve. For example, the valve anchor could appear properly seated on the ultrasound image, but the side of the valve anchor not visible in the image could be misaligned and/or improperly sealed with the lumen wall. As described, a slightly improper seal or slight misplacement of the valve anchor can lead to catastrophic and even fatal results. Additionally, once the replacement valve has been fully deployed, it is difficult or impossible to change the position of the prosthesis without damaging the native structure.

As a result of the limitations of both bioprosthetic heart valve and mechanical valves, patients have to choose between quality of life and durability of the repair. Additionally there is a group of patients which may not tolerate the risks associated with a mechanical valve, but may limit their lives using a bioprosthetic valve as a second operation to replace this valve can be considered clinically not viable.

Therefore, it would be advantageous to provide an apparatus and method to prepare a deficient native valve for replacement.

Additionally, it would be advantageous to provide an apparatus and method for accurate and efficacious deployment of a valve anchor.

Additionally, it would be advantageous to provide an apparatus and method for accurate and efficacious deployment of a valve anchor independent of a replacement heart valve.

Additionally, it would be advantageous to provide an apparatus and method for correcting valvular heart disease that allows for accurate and efficacious deployment of a heart valve prosthesis.

Additionally, it would be advantageous to provide an apparatus and method for correcting valvular heart disease that allows for viable methods to conduct repeat operations on a heart valve.

Additionally, it would be advantageous to provide an apparatus and method for correcting valvular heart disease that allows for viable methods to replace a previously deployed heart valve prosthesis.

Additionally, it would be advantageous to provide an apparatus and method for correcting valvular heart disease that allows for deployment of a replaceable heart valve prosthesis implemented in a minimally invasive manner.

Additionally, it would be advantageous to provide a releasably connected heart valve prosthesis delivered with a long arm or steerable needle from outside the heart to a valve of a beating heart.

Additionally, it would be advantageous to provide a smooth and substantially uniform surface within a lumen for deployment of a heart valve prosthesis.

Additionally, it would be advantageous to provide a backup system capable of permitting a patient to go on bypass if a heart valve replacement procedure fails.

Additionally, it would be advantageous to provide an apparatus capable of providing a separately deployable harbor for releasably connecting a heart valve prostheses.

BRIEF SUMMARY OF THE INVENTION

The present invention describes methods and apparatus to prepare a heart valve for replacement and improve a deficient heart valve. An exemplary embodiment of the method of preparing a heart valve for replacement involves delivering an anchoring conduit to a heart valve. The anchoring conduit is expanded in the heart valve and the expansion of the anchoring conduit disables the heart valve. Furthermore, the expansion of the anchoring conduit defines an open cavity.

An exemplary embodiment of the method of improving a deficient heart valve involves delivering an anchoring conduit to a heart valve. The anchoring conduit has a harbor, which is enabled to releasably connect a heart valve prosthesis. Then, a temporary valve is delivered in a condensed state to a target site in an artery proximate the heart valve. Subsequently, the anchoring conduit is deployed in the heart valve, disabling the heart valve. The temporary valve operates to temporarily replace the function of the heart valve when the anchoring conduit is expanded.

These and other objects, features and advantages of the present invention will become more apparent upon reading the following specification in conjunction with the accompanying drawing figures.

DETAILED DESCRIPTION OF PREFERRED EMBODIMENTS

Figure 1:
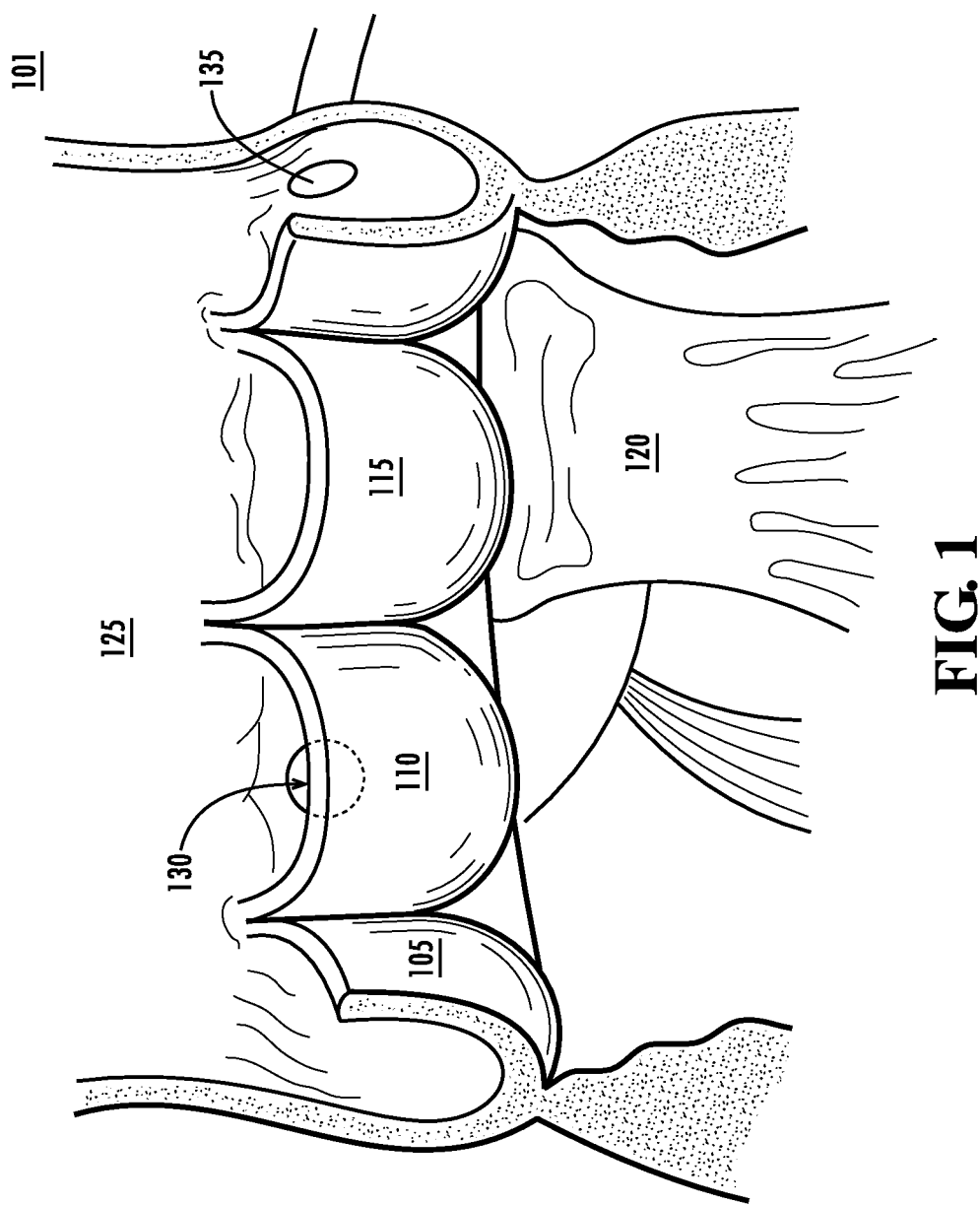
FIG. 1 provides an illustration of a normal aortic valve 101.

The present invention addresses the deficiencies in the prior art by providing a minimally invasive apparatus and method for preparing a heart valve for replacement and for deploying a replaceable heart valve prosthesis. The apparatus and method of preparing a heart valve for replacement can be used to improve the success and efficacy of heart valve repair. The medical device and method of improving a deficient heart valve disclosed herein can be used to repeatedly deploy a heart valve prostheses within a deficient valve of the heart. Enabling the efficacious replacement of a heart valve can provide an effective manner of treating valvular heart disease without many of the drawbacks associated with conventional devices and methods. Significantly, the cardiac prosthesis system of the present invention provides a solution which does not force patients to choose between the quality of life associated with bioprosthetic valves and long term durability associated with mechanical valves. Additionally, this procedure can allow beating heart minimally invasive approaches which can benefit the clinical outcome of heart valve replacements.

An exemplary embodiment of the present invention provides a method of preparing a heart valve for replacement. The method involves the step of delivering an anchoring conduit to a heart valve. Subsequently, the anchoring conduit is expanded in the heart valve. Once the anchoring conduit has been expanded, it defines an open cavity.

In an exemplary embodiment, the open cavity does not contain any leaflets or other elements of a heart valve prosthesis. Furthermore, in an exemplary embodiment, the open cavity has a substantially uniform inner surface. The term substantially uniform is used herein to describe a surface that is generally uniform but may include certain undulations or features. For example, the term substantially uniform surface of the open cavity of the anchoring conduit could describe a cavity that includes a releasably engaging component. Therefore, the substantially uniform surface of the cavity is generally uniform, but not entirely uniform in some embodiments.

The smooth and substantially uniform inner surface of the exemplary embodiment of the expanded form of the anchoring conduit provides a more safe and reliable surface on which to deploy a heart valve prosthesis. Typically, a deficient native valve and the areas of tissue around the native valve have irregularities and heavy calcification. The common calcification, thickening, and hardening of the cardiac annulus can make it increasingly difficult to achieve proper sealing quality for a valve anchor. For example, the existing annulus of the deficient native valve can have a surface that is to varying degrees irregular and calcified, which not only lessens the quality of the support of the anchoring conduit but also acts as a source of leaks between the anchoring conduit and the valve annulus. The exemplary embodiment of the present invention can provide an anchoring conduit to aid in the placement of a heart valve prosthesis and overcome the complexities associated with the irregular and calcified surface of a deficient valve annulus. The smooth and substantially uniform inner surface of the anchoring conduit, as opposed to the bumpy and calcified surface of native valve, can enable a more efficacious and reliable deployment of a replaceable heart valve. An exemplary embodiment of the anchoring conduit is capable of deployment independent of the deployment of the heart valve prosthesis. Furthermore, the quality of the seating of the anchoring conduit can be assessed and verified prior to the introduction of the heart valve prosthesis into the patient's body.

An exemplary embodiment of the present invention also provides a method of improving a deficient heart valve. The method first involves delivering an anchoring conduit to a heart valve. The anchoring conduit has a harbor, which is enabled to releasably connect a heart valve prosthesis. A temporary valve is delivered in a condensed state to a target site in an artery proximate the heart valve. The temporary valve can be expanded at the target site in the artery proximate the heart valve. Subsequently, the anchoring conduit can be expanded in the heart valve and the native components of the heart valve compress against the heart valve and disable the heart valve. The temporary valve can operate to temporarily replace the function of the heart valve when the anchoring conduit is expanded.

Furthermore, the present invention enables a cardiac prosthetic system capable improving a deficient heart valve. In an exemplary embodiment, the deficient heart valve can either be a native valve in the heart or heart valve prosthesis previously deployed in the heart. An exemplary embodiment of the cardiac prosthetic system in accordance with the present invention provides an anchoring conduit having a harbor. The harbor includes a first releasably engaging component. Furthermore, the cardiac prosthetic system provides a temporary valve. Additionally, a heart valve prosthesis is provided, having a second releasably engaging component enabled to be securely coupled and uncoupled from the first releasably engaging component of the harbor.

Figure 2:
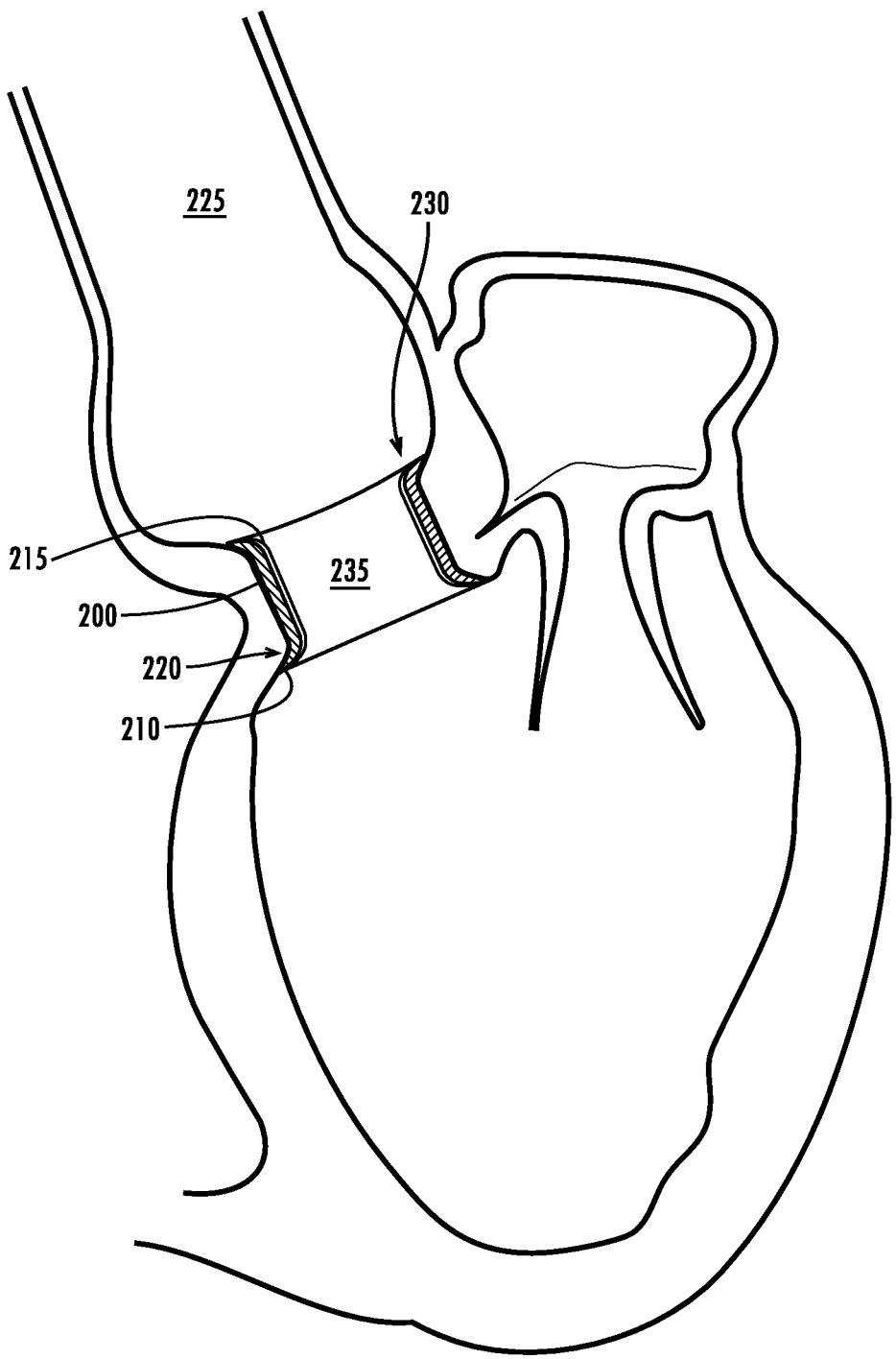
FIG. 2 provides an illustration of an exemplary embodiment of an anchoring conduit 200 implemented in aortic valve in accordance with an exemplary embodiment of the present invention.

FIG. 2 provides an illustration of an exemplary embodiment of an anchoring conduit 200 implemented in an aortic valve in accordance with an exemplary embodiment of the present invention. As shown in FIG. 2, the anchoring conduit provides an expandable structure with a proximal anchor component 210 and a distal anchor component 215. In an exemplary embodiment, the expansion of the anchoring conduit 200 enables the proximal anchor component 210 and the distal anchor component 215 to interface with a tissue component and define an open cavity 235 with a substantially uniform inner surface.

The terms proximal and proximate are used herein to describe a position which is in the relative vicinity of another position, including a range of vicinity positions through and including being directly adjacent or abutting another position. The term distal is used herein to describe a position which is situated a relative distance away from another position. Thus, the terms proximal/proximate and distal are used herein as spatial relation references and are not used to describe positions upstream or downstream in the flow of blood.

In the exemplary embodiment depicted in FIG. 2, the anchoring conduit 200 is deployed in an aortic valve 220. The anchoring conduit 200 can be delivered in unexpanded state, thereby enabling endovascular delivery or other minimally invasive forms of deployment. Thus, in an exemplary embodiment, the anchoring conduit 200 can be percutaneously deployed via a catheter to the site of the aortic valve 220. Once the surgeon, has delivered to the anchoring conduit 200 in a collapsed state to the desired location within the aortic valve 220, the anchoring conduit 200 can then be expanded. It is this expansion of the anchoring conduit 200 that causes the proximal anchor component 210 to engage the lumen wall within the aorta 225. In the exemplary embodiment shown in FIG. 2, the anchoring conduit 200 is positioned such that the proximal anchor component 210 engages the aortic valve 220 proximate the annulus of the aortic valve 220. In this manner, the proximal anchor component 210 serves to collapse the cusps of the aortic valve 220 against the lumen wall of the aorta 225. Thereby, the expansion of the anchoring conduit 200 may disable the native aortic valve 220.

The expansion of the anchoring conduit 200 also serves to engage the distal anchor component 215 with the lumen wall of the aorta 225. As shown in the exemplary embodiment of FIG. 2, the distal anchor component 215 can be positioned to engage the aorta 225 proximate the sinuses of the valsalva 230. In an exemplary embodiment, the anchoring conduit 200 can be configured to conform to the shape of the sinuses of the valsalva 230 and thus aid in locking the anchoring conduit 200 into place. In an alternative embodiment, the distal anchor component 215 of the anchoring conduit 200 can be provided with hooks capable of piercing the lumen wall proximate the sinuses of the valsalva 230. The piercing of the lumen wall can aid in locking the anchoring conduit 200 in place.

An important advantage provided by an exemplary embodiment of the anchoring conduit 200 is that it can enable independent deployment of the valve anchor separate from the deployment of a valve prosthesis. The independent deployment of the anchoring conduit 200 can help the surgeon avoid and minimize numerous risks involved in repairing a deficient heart valve. Conventional devices involve the percutaneous deployment of one device containing both the valve anchor and the valve prosthesis. Most often, the surgeon conducting a minimally invasive procedure is visually aided only by the two-dimensional sonographic image of an ultrasound. Thus, the surgeon is faced with the task of attempting to precisely implement a three-dimensional device with only two-dimensional feedback. When using a conventional device, the surgeon essentially has "one shot" to perfectly deploy the device.

The risks associated with the conventional "one shot" approach of percutaneous heart valve replacement are numerous and alarming. Unfortunately, many procedures performed with conventional devices have been unsuccessful and even fatal. A large risk associated with percutaneous deployment is that when the valve anchor of the conventional device is implemented on the hardened and calcified surface of the native valve, it can be loosely seated. A relatively loose seating of the conventional valve device may ultimately lead to migration of the device or leakage between the device and the lumen wall. Moreover, an additional risk results from the fact that the placement of the conventional device can breakup the calcium deposits on the deficient heart valve and release these deposits into the bloodstream. All of these risks are associated with the deployment of a conventional valve device. An exemplary embodiment of the anchoring conduit 200, however, can help to minimize and avoid a number of these risks.

Contrary to conventional devices, the anchoring conduit 200 can contain only the anchoring components and inner lumen. The independent implementation of the anchoring conduit 200 permits the surgeon to concentrate on the variables involved in correctly and securely deploying the anchoring conduit 200 without concern for the placement or function of the replacement heart valve prosthesis. Therefore, the independent deployment of the anchoring conduit 200 can help to minimize the number of variables that the surgeon must control in deploying such a device. Furthermore, if the surgeon fails to correctly implement the anchoring conduit 200, the surgeon can then implement certain procedures to correct the placement of the anchoring conduit 200 or extract the failed area where the anchoring conduit 200 was positioned. For example, and not limitation, should the placement of the anchoring conduit 200 fail, the patient can by placed on bypass and the failed aortic root can be replaced with an aortic root conduit.

As shown in FIG. 2, when the anchoring conduit 200 is been deployed in the aortic valve 220, an open cavity 235 is created. This open cavity 235 can have a smooth and substantially uniform surface. This smooth and substantially uniform surface can replace the calcified, hardened, and rough surface of the deficient aortic valve 220. The smooth and substantially uniform surface of the cavity 235 of the anchoring conduit 200 provides many advantages. Significantly, the smooth and substantially uniform surface of the cavity provides a greatly improved area for deploying a heart valve prosthesis. Conventional devices are often unsuccessful due to the necessity of anchoring the device on a non-uniform surface. Valve prosthesis deployed in accordance with an embodiment of the present invention can be enabled to be deployed on the substantially uniform inner surface of the anchoring conduit 200.

In an exemplary embodiment the anchoring conduit 200 is composed of a thread-like structure that can be made of stainless steel, titanium, similar metals or metal alloys, or suitable plastics. These thread-like structures or filaments can be latticed looped or wound. In one embodiment, the anchoring conduit 200 composed of a surgical stainless steal mesh. In some embodiments, the anchoring conduit 200 is composed of a shape memory material, such as a nickel-titanium alloy. The anchoring conduit 200 can be composed of a material capable of bending into the surface of the lumen wall against which it is anchored. As the native inner lumen is often an irregular and hard surface, is advantageous for the anchoring conduit 200 to be enabled to bend and conform to the shape of the native lumen wall against which it is anchored so as to ensure safe and secure seating of the anchoring conduit 200. Additionally, an embodiment of the anchoring conduit 200 may include a biocompatible lumen. In this embodiment, the thread-like structure provides the outer core and its hollow interior can be lined with a biocompatible lumen. In some embodiments, the anchoring conduit 200 can provide an outer layer capable of bending to conform to the native lumen wall, and an inner layer which maintains a substantially uniform and smooth surface.

In alternative embodiments to that depicted in FIG. 2, the anchoring conduit 200 can be deployed in other areas of the aorta 225. For example, and not limitation, the anchoring conduit 200 can be expanded such that the proximal anchor component 210 of the anchoring conduit 200 interfaces with the lumen wall of the aorta 225 proximate the sino-tubular junction. Therefore, the anchoring conduit 200 can be deployed further down on the aortic root. Additionally, the anchoring conduit 200 can be deployed further up the aorta, such as above the sinuses of the valsalva 230 or even proximate the aortic arch. Additionally, the anchoring conduit 200 can be deployed in valves other than aortic valve. In an exemplary embodiment, the anchoring conduit 200 can be deployed in a pulmonic valve.

Figure 3:
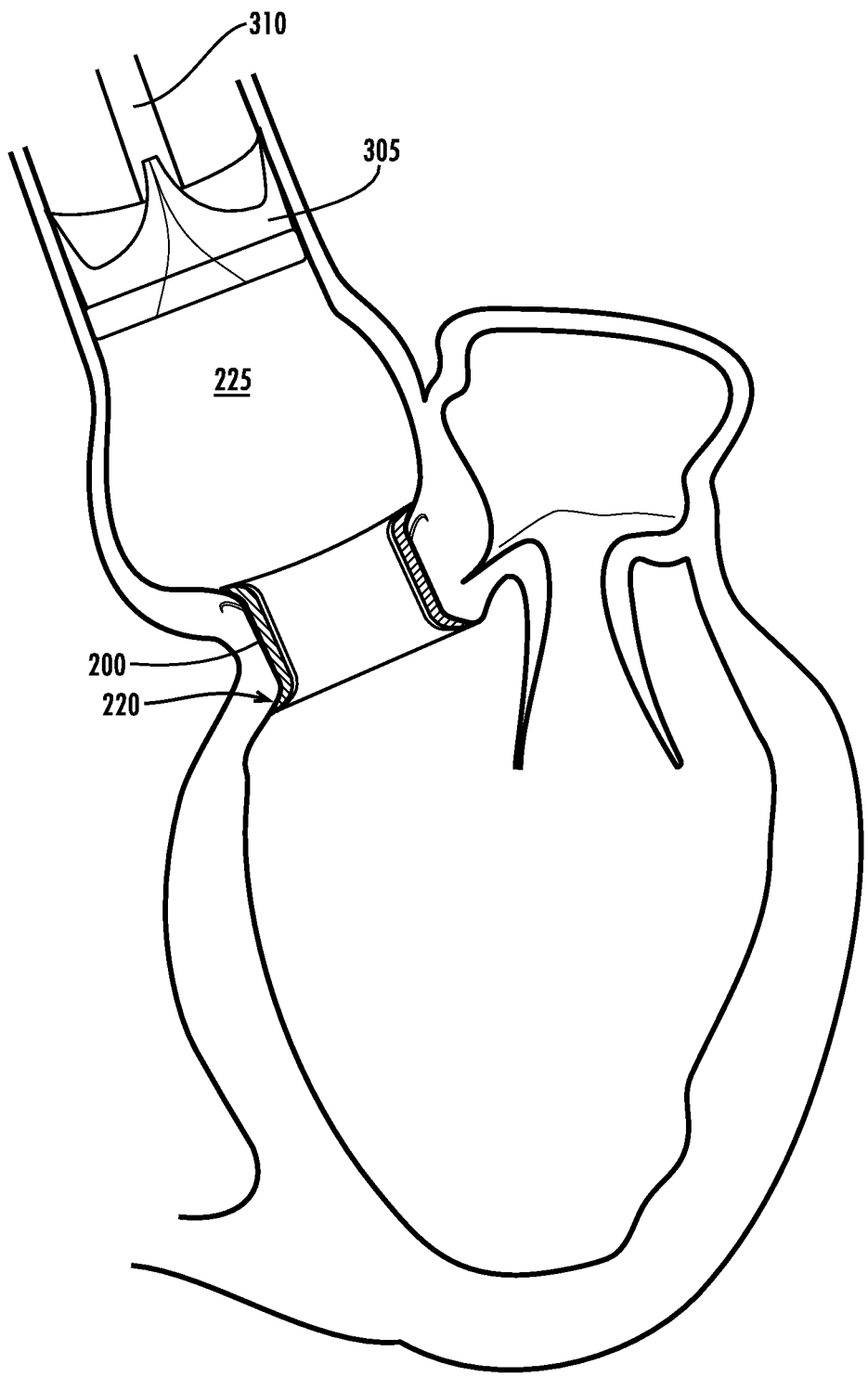
FIG. 3 provides an illustration of an exemplary embodiment of anchoring conduit 200 and temporary valve 305 implemented in an aortic valve in accordance with an exemplary embodiment of the present invention.

FIG. 3 provides an illustration of an exemplary embodiment of anchoring conduit 200 and temporary valve 305 implemented in an aortic valve in accordance with an exemplary embodiment of the present invention. As shown in FIG. 3, the anchoring conduit 200 can be deployed in the aortic valve 220 such that the aortic valve 220 is disabled. More particularly, the expansion of the anchoring conduit 200 serves to collapse the cusps of the native aortic valve 220 and thus it ceases to function. In an exemplary embodiment of the present invention, a temporary valve 305 can be implemented to temporarily replace the function of this disabled heart valve.

The temporary valve 305, in the exemplary embodiment shown in FIG. 3, can be a mechanical or bioprosthetic valve. The temporary valve 305 can be deployed in a minimally invasive manner, such as attached to a catheter 310 shown FIG. 3. The temporary valve 305 can be initially collapsed while it is delivered to its functional location. When the temporary valve 305 is in its functional location, it can then be expanded. When the temporary valve 305 expands, it is pushed or sealed against the lumen wall of the aorta 225. In an exemplary embodiment the temporary valve 305 does not attach to the wall of the aorta 225. Once the temporary valve 305 is expanded, its cusps can open and close controlling the flow of blood through the aorta 225. Therefore, the temporary valve 305 can be delivered before the native valve is rendered non-functional. Thus, once the native valve is rendered non-functional, the temporary valve 305 can perform the function of the native valve without interrupting the cardiac cycle of the beating heart.

Figure 4A:
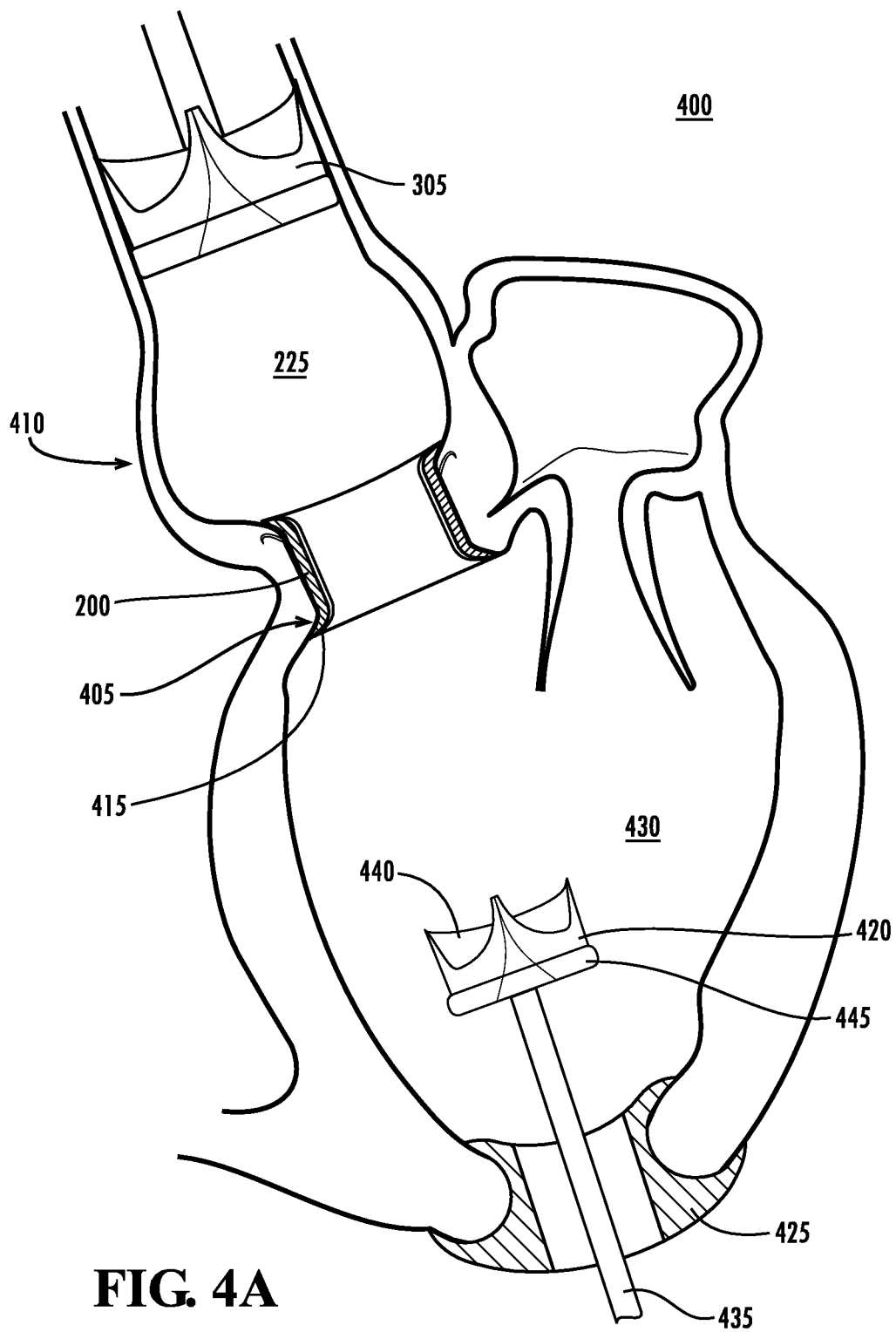
FIG. 4A provides an illustration of an exemplary embodiment of a cardiac prosthetic system 400 implemented in aortic valve in accordance with an exemplary embodiment of the present invention.

FIG. 4A provides an illustration of an exemplary embodiment of a cardiac prosthetic system 400 implemented in aortic valve in accordance with an exemplary embodiment of the present invention. As shown in FIG. 4A, the anchoring conduit 200 can be deployed in the aortic root proximate the aortic annulus. In an exemplary embodiment, the anchoring conduit 200 covers the inlet area between the left ventricle 430 and the aorta 225. In one embodiment, the anchoring conduit 200 can cover an area immediately proximate the aortic annulus 405.

In an exemplary embodiment shown in FIG. 4A, the anchoring conduit 200 can delivered in a condensed form. For example, and not limitation, the anchoring conduit 200 can be composed of a surgical stainless mesh that is capable of being collapsed. The collapsed anchoring conduit 200 is capable of delivery in a minimally invasive manner, including via percutaneous deployment or a long arm delivery device. In an exemplary embodiment, an anchoring conduit 200 is delivered minimally invasively through a heart chamber or the arterial/venous system into the aortic root 410. Once the collapsed anchoring conduit 200 is delivered to the desired location in the base of the aortic root 410 it can be expanded and anchored into the aortic root 410. In an exemplary embodiment, the anchoring conduit 200 can be expanded proximate the aortic annulus 405. In another embodiment, the anchoring conduit 200 can be expanded further into the aortic root 410. Additionally, in an alternative embodiment, the steps of the methods of the present invention can be implemented via a remote device. For example, and not limitation, a surgeon could be enabled to use a remote device to expand the anchoring conduit 200 once delivered to the desired position.

In an exemplary embodiment, the anchoring conduit 200 provides a harbor 415. The harbor 415 can include a releasably engaging component, which is enabled to serve as a receiving port for a heart valve prosthesis. This releasably engaging component, in an exemplary embodiment, is enabled to couple with a mating releasably engaging component of heart valve prosthesis 420. The heart valve prosthesis 420 can be a variety of different types of heart valve prostheses, including various types of mechanical valves and bioprosthetic heart valves.

The implementation of the anchoring conduit 200 renders the native valve non-functional, therefore, an exemplary embodiment of the present invention provides a temporary valve that can be placed in the aorta 225 to perform the function of the native valve. The temporary valve 305, in the exemplary embodiment shown in FIG. 4A, can be a mechanical or bioprosthetic valve. The temporary valve 305 can be deployed in a minimally invasive manner, such as attached to a catheter 310 shown FIG. 4A. Therefore, the temporary valve 305 can be delivered before the native valve is rendered non-functional. Once the native valve is rendered non-functional, the temporary valve 305 can perform the function of the native valve without interrupting the cardiac cycle of the beating heart being repaired.

When both the anchoring conduit 200 and the temporary valve 305 are in place, the heart valve prosthesis 420 can be introduced into the heart. In an exemplary embodiment shown in FIG. 4A, the heart valve prosthesis 420 is introduced through a port 425 in the heart chamber. In an alternative embodiment, the heart valve prosthesis 420 can be introduced through the venous/arterial system. The port 425 in the exemplary embodiment depicted in FIG. 4A is mounted on the lower wall of the left ventricle 430 and provides an orifice through which the heart valve prosthesis 420 can be delivered. Those of skill in the art will appreciate that port 425 could be a variety of different ports know in the art. The heart valve prosthesis 420 can be delivered via a catheter or long arm device, or other minimally invasive apparatus. The heart valve prosthesis 420 of the exemplary embodiment shown FIG. 4A is delivered via long arm device 435.

In the exemplary embodiment depicted in FIG. 4A, once the heart valve prosthesis 420 has been introduced into the left ventricle 430, it can be delivered to a harbor 415 on the anchoring conduit 200. In an exemplary embodiment, the heart valve prosthesis 420 includes a plurality of leaflets 440. These leaflets 440 can function to replace the action of deficient heart valve. Additionally, the heart valve prosthesis 420 provides an annulus ring 445. The annulus ring 445 is capable of interfacing with the anchoring conduit 200 to provide a proper seal for the heart valve prosthesis 420. The heart valve prosthesis 420 may be stented or stentless according to needs of particular implementation.

In an exemplary embodiment, the heart valve prosthesis 420 can provide a releasably engaging component. This releasably engaging component is enabled to couple and uncouple to a mating releasably engaging component provided on harbor 415. The releasably engaging component of the heart valve prosthesis 420 can be positioned at various locations on the device to ensure proper mating with the harbor 415. This releasably engaging component may be on the annulus or stent portion of the heart valve prosthesis 420. Once the heart valve prosthesis 420 has been mated to the releasably engaging component of the harbor 415 of the anchoring conduit 200, the harbor 415 can releasably retain the heart valve prosthesis 420 in place, and the heart valve prosthesis 420 can be released from the catheter or long arm.

After heart valve prosthesis 420 is deployed, the temporary valve 305 can be extracted. Furthermore, the ports in the venous/arterial system or ports in the heart can be closed using a mechanism which can allow them to be opened when the heart valve needs to be replaced.

When a heart valve prosthesis 420 fails or reaches a limit in it functional life, the ports in the arterial/venous system and the heart chambers can be reopened to deliver a new heart valve prosthesis to the harbor 415 in the anchoring conduit 200. Again, a temporary valve 305 can be placed in the aorta 225 to control blood flow. Then, a catheter or long arm can be used to engage the old heart valve prosthesis 420 on the anchoring conduit 200. The heart valve prosthesis 420 can then be uncoupled from the releasably engaging component of the harbor 415 and the old heart valve prosthesis 420 can be extracted. A new heart valve prosthesis can subsequently be introduced into the left ventricle 430, via a catheter or long arm mechanism, and releasably engaged to the harbor 415 of anchoring conduit 200. Thus, the deficient heart valve prosthesis can be replaced with a new heart valve prosthesis in a minimally invasive manner. The above process may be repeated one or several times over the life of the patient according to clinical requirements.

Figure 4B:
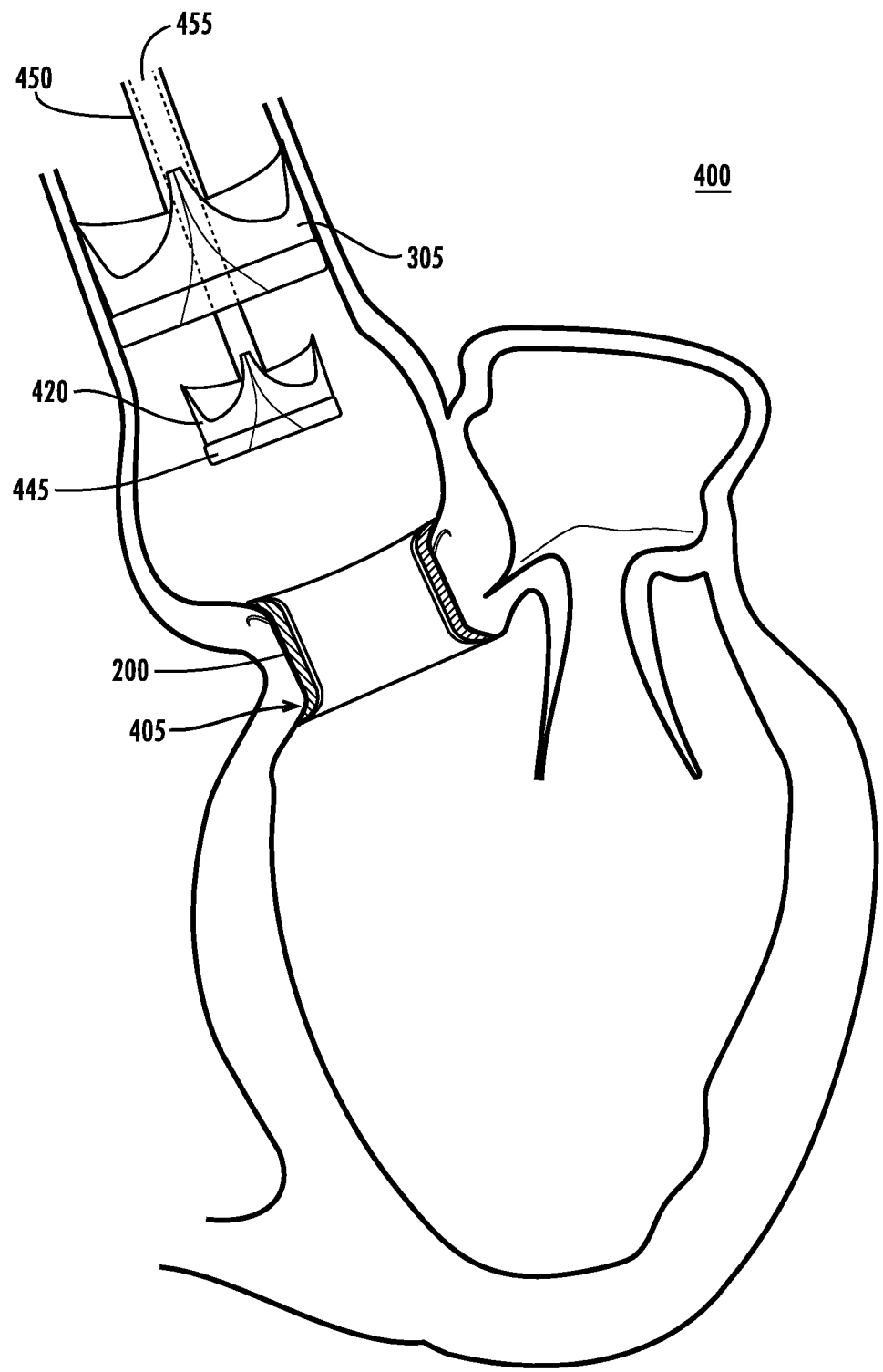
FIG. 4B provides an illustration of an alternative embodiment of a cardiac prosthetic system 400 implemented in aortic valve in accordance with an exemplary embodiment of the present invention.

FIG. 4B provides an illustration of an alternative embodiment of a cardiac prosthetic system 400 implemented in aortic valve in accordance with an exemplary embodiment of the present invention. In the alternative embodiment depicted in FIG. 4B, the heart valve prosthesis 420 is delivered via a conduit in the temporary valve 305. In the alternative embodiment shown in FIG. 4B, the temporary valve 305 is delivered via an enlarged catheter 450 which provides an internal conduit 455. The internal conduit 455 enables a path through which a heart valve prosthesis 420 can be delivered in accordance with an exemplary embodiment of the cardiac prosthetic system 400.

As shown in FIG. 4B, the alternative embodiment of the heart valve prosthesis 420 is enabled to passed through the center of the temporary valve 305. Thereby, in accordance with a method of improving a deficient heart valve of the present invention, the temporary valve 305 can be deployed to temporarily perform the function of the deficient aortic valve 220. The anchoring conduit 200 can then be properly seated and secured within the deficient aortic valve as shown in FIG. 4B. After it is verified that the anchoring conduit 200 has been properly placed, the heart valve prosthesis 420 can then be delivered to the aorta 225 via the internal conduit 455 of the enlarged catheter 450. In an exemplary embodiment, the heart valve prosthesis 420 is capable of delivery in a collapsed form, such that it can be passed through the internal conduit 455. Once the heart valve prosthesis 420 has entered the aorta 225, it can be expanded into functional form. Thereafter, the heart valve prosthesis 420 can be deployed in the anchoring conduit 200.

In the embodiment depicted in FIG. 4B, a releasably engaging component on the heart valve prosthesis 420 can be coupled to a mating releasably engaging component on the harbor 415 of the anchoring conduit 200. In an alternative embodiment, the heart valve prosthesis 420 can be provided without a releasably engaging component. In this alternative embodiment, the heart valve prosthesis 420 can simply be expanded within the anchoring conduit 200 such that the annulus 445 of the heart valve prosthesis 420 interfaces with the smooth inner surface of the anchoring conduit 200. Those of skill in the art will appreciate that the heart valve prosthesis 420 could be delivered and deployed in a number of different manners without detracting from the scope of the invention.

An additional alternative embodiment of the cardiac prosthetic system 400 enables an alternative method for the delivery of the anchoring conduit 200. In this embodiment, the anchoring conduit 200 is enabled to be delivered through the internal conduit 455 of the enlarged catheter 450 shown in FIG. 4B. Thus, the method of improving a deficient heart valve implemented with this embodiment can first involve the delivery and deployment of the temporary valve 350 to an area proximate the deficient heart valve. Next, the anchoring conduit 200 can be permitted to pass through the internal conduit 455 of the enlarged catheter 450 of the deployed temporary valve 305. Thus, the anchoring conduit 200 can be delivered by catheter in a compressed state through the temporary valve 305. The anchoring conduit 200 can then be positioned proximate the deficient heart valve and deployed. After the anchoring conduit 200 is successfully deployed, the catheter that delivered the anchoring conduit 200 can be removed. Subsequently, a heart valve prosthesis 420 can be delivered through the internal conduit 455 of the enlarged catheter 450 of the deployed temporary valve 305.

Figure 5A:
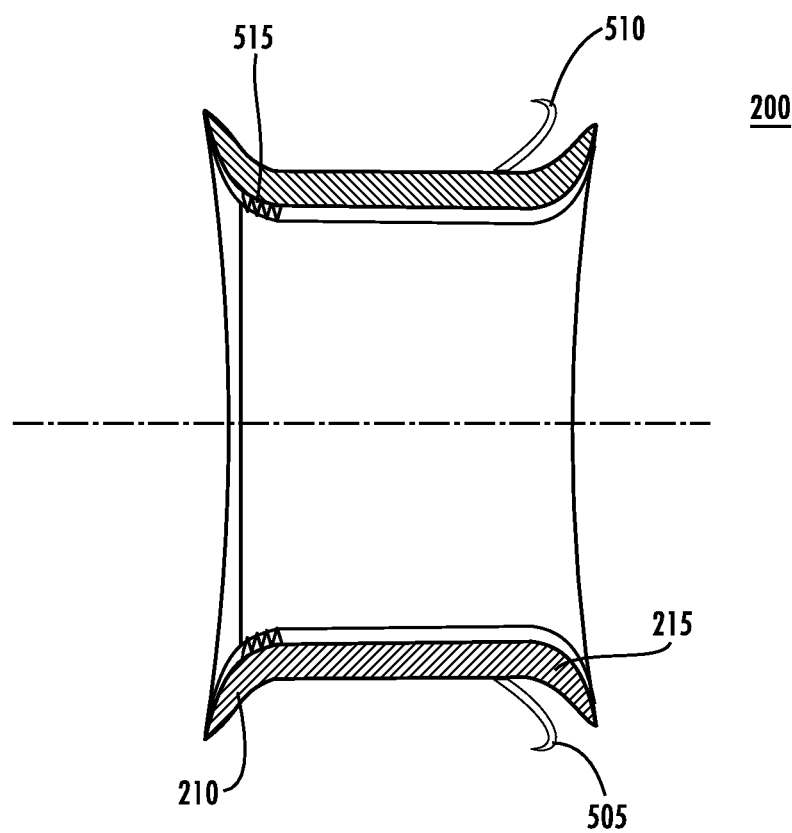
FIG. 5A provides an illustration of an exemplary embodiment of an anchoring conduit 200 in accordance with an exemplary embodiment of the present invention.

FIG. 5A provides an illustration of an exemplary embodiment of an anchoring conduit 200 in accordance with an exemplary embodiment of the present invention. The anchoring conduit 200 has a proximal anchor component 210 and a distal anchor component 215. The proximal anchor component 210 can be anchored into a lumen wall. In the exemplary embodiment depicted in FIG. 5A, the proximal anchor component 210 has a flared edge which serves as a seal preventing leaks between the aortic root and the walls of the anchoring conduit 200. In an exemplary embodiment, the distal anchoring edge 215 is contoured to the shape of the sinuses of the valsalva 230. In this exemplary embodiment, the distal anchoring edge 215 is configured to engage the surface of the sinuses of the valsalva 230 and further secure the anchoring conduit 200 into place.

Additionally, the exemplary embodiment of the anchoring conduit 200 shown in FIG. 5A provides tissue piercing components 505 and 510. The tissue piercing components 505 and 510 are enabled to pierce and engage a tissue component, and, thus, aid in stabilizing the anchoring conduit 200. In the exemplary embodiment shown in FIG. 5A, the piercing components 505 and 510 of the distal anchor component 220 flare into the sinuses of valsalva and help to secure the anchoring conduit 200 into place. Those of skill in the art will appreciate that the piercing components 505 and 510 can be hooks or other types of anchors sufficient to engage a tissue component in the heart. The expansion into the sinuses may have a lumen in order to prevent blood migration between the conduit and the aortic wall. In an exemplary embodiment, the anchoring 200 provides an outer surface for mating with the irregularities of the surface to which the anchoring conduit 200 is seated and a substantially uniform inner surface. Thereby, the smooth and substantially uniform inner surface of the anchoring conduit 200 is not effected by the undulations impressed in the seated outer surface of the anchoring conduit 200.

As shown in FIG. 5A, and exemplary embodiment of the anchoring conduit 200 can provide a releasably engaging component 515. The releasably engaging component 515 can be many suitable components capable of enabling the coupling and uncoupling of a heart valve prosthesis 420. The releasably engaging component 515 shown in the exemplary embodiment in FIG. 5A is comprised of threading. Thus, the proximal anchor component 210 can provide a series of threading for the releasably engaging component 515. Coupling of the heart valve prosthesis 420 can then be accomplished, in the exemplary embodiment, by attaching a mating releasably engaging component of the heart valve prosthesis 420 with appropriate counter threading. Therefore, the method of improving a deficient heart valve in accordance with the present invention can involve the coupling of heart valve prosthesis 420 to the threading of the releasably engaging component 515 of the anchoring conduit 200. Those of skill in the art will appreciate that number of different devices, components, and mechanisms could be substituted for the threading of the releasably engaging component 515 shown in FIG. 5A without detracting from the invention. For example, and not limitation, the releasably engaging component 515 could be a series of groves in which mating prongs can be inserted, an orifice through which an expanding toggle component can be inserted, a magnetic system, clamps, a latching mechanism, or other suitable component.

Figure 5B:
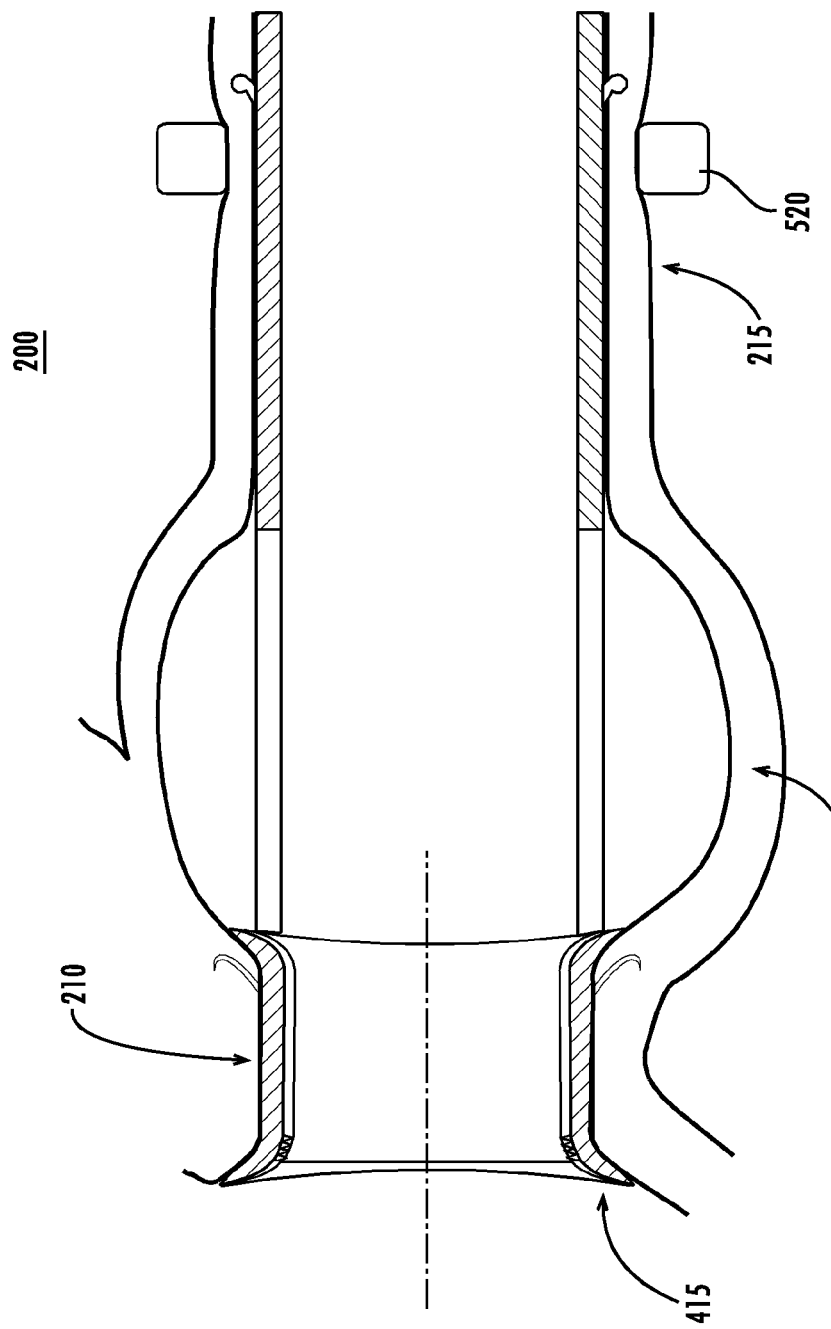
FIG. 5B provides an illustration of an exemplary embodiment of an anchoring conduit 200 in accordance with an exemplary embodiment of the present invention.

FIG. 5B provides an illustration of an exemplary embodiment of an anchoring conduit 200 in accordance with an exemplary embodiment of the present invention. In the exemplary embodiment depicted in FIG. 5B, the anchoring conduit 200 traverses the sinuses of the valsalva 230. As previously described in relation to FIG. 1, the sinuses of the valsalva 230 are located just above the three cusps, 105, 110, and 115 (FIG. 1) and each sinus corresponds to each individual cusp. Proximate the sinuses of the valsalva 230 are the origins of the coronary arteries. The anchoring conduit 200 can provide openings proximate the sinuses of the valsalva so as not to interrupt the openings to the coronary arteries and allow for the free flow of blood. In the exemplary embodiment shown in FIG. 5B, the distal anchor component 215 of the anchoring conduit 200 may also extend beyond the sinuses of valsalva 230 and anchor into the aortic wall below the aortic arch, as shown in FIG. 5B.

In the exemplary embodiment shown in FIG. 5B, an external aortic ring 520 may be releasably placed on the external surface of the aortic root in order to aid in locking the anchoring conduit 200 in place. In this embodiment, the distal anchor component 210 of anchoring conduit 200 protrudes radially outward against the lumen wall. The aortic ring 520 can then deployed below the protrusions in the distal anchor component 350 of the anchoring conduit 200, and thereby prevent the anchoring conduit 200 from migrating past the aortic ring 520.

The exemplary embodiment of the anchoring conduit 200 shown in FIG. 5B provides a proximal anchor component 210. The proximal end 210 can contain a harbor 415. The harbor 415 can enable the releasable connection of a heart valve prosthesis. The harbor 415 in the exemplary embodiment in FIG. 5B is placed on the proximal anchor component 210 of the anchoring conduit 200. In another embodiment, the harbor 415 may be located in the normal position of the native valve. In an alternative embodiment, the harbor 415 can be located in the distal anchor component 215 of the anchoring conduit 200. The harbor 415 can provide a releasably engaging component. Those of skill in the art will appreciate that many different types of releasably engaging components could be incorporated into the harbor 415 to accomplish the necessary function.

Figure 6:
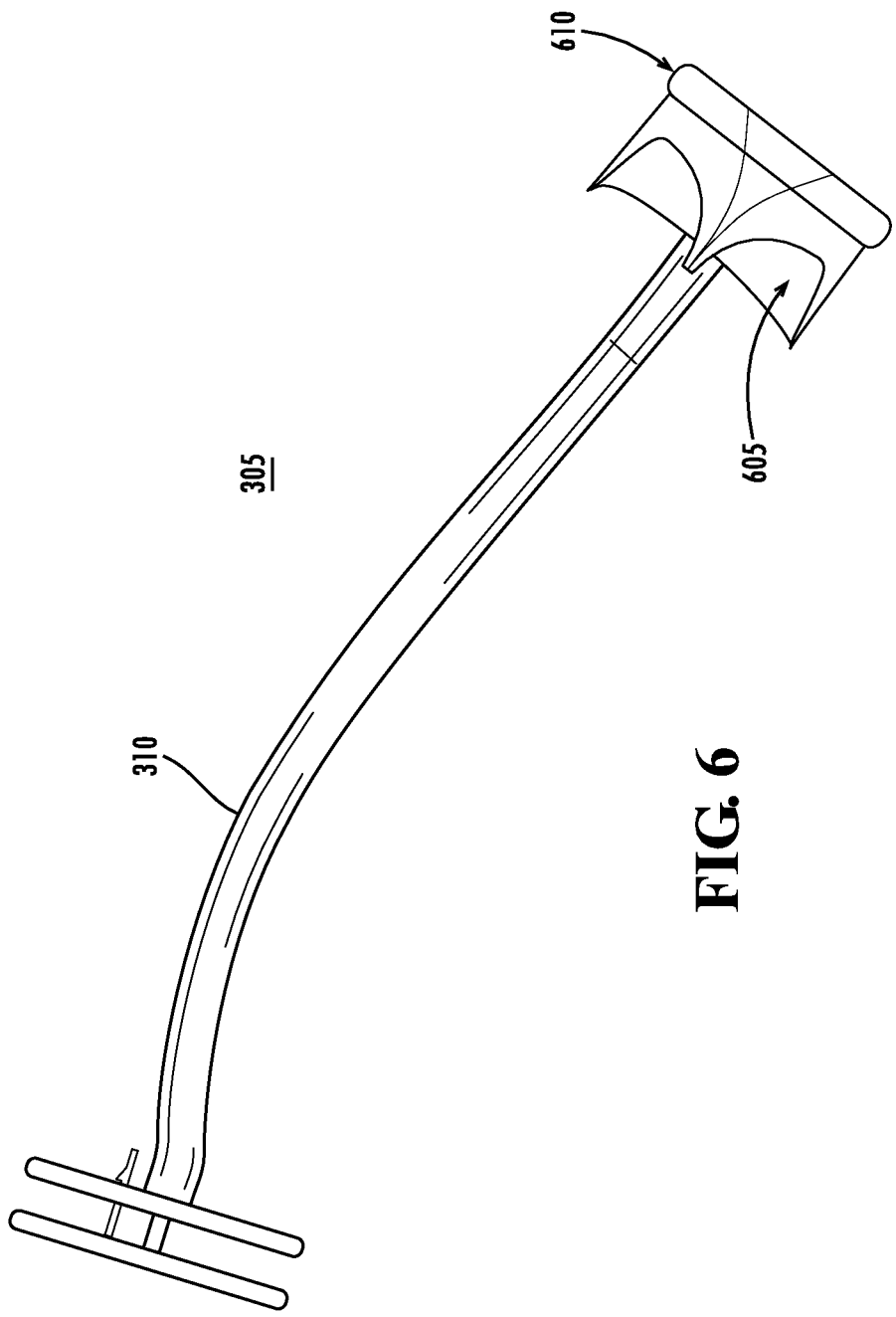
FIG. 6 provides an illustration of an exemplary embodiment of a temporary valve 305 in accordance with an exemplary embodiment of the present invention.

FIG. 6 provides an illustration of an exemplary embodiment of a temporary valve 305 in accordance with an exemplary embodiment of the present invention. The temporary valve 305 is includes a single or plurality of leaflets within a collapsible frame. In the exemplary embodiment shown in FIG. 4, the leaflets 605 can be constructed of biocompatible materials. In a non-limiting example, a biocompatible polymer material is used to create the leaflets 605. In an alternative embodiment, the leaflets 605 of the temporary valve 305 can be constructed from bovine pericardium. In yet another embodiment, the leaflets 605 of the temporary valve 305 can be constructed from porcine aortic leaflets. Additionally, the leaflets 605 of the temporary valve 305 can be constructed from metallic materials such as carbon or other metals. Those of skill in the art will appreciate that the temporary valve 305 can be a number of different types of valves capable of temporary deployment into the heart.

In the exemplary embodiment depicted in FIG. 4, the collapsible frame 610 of the temporary valve 305 may be constructed of a biocompatible polymer structure. In another embodiment, the collapsible frame 610 may be constructed using a doughnut shaped balloon, where the balloon is constructed of a polymer. Alternatively, an embodiment of the collapsible frame 610 may be constructed of a memory alloy or memory polymer mesh.

As shown in FIG. 6, the collapsible frame 610 can be attached to a polymer catheter 615 for delivery to the desired location within the heart. Typically the collapsible frame 610 is permanently connected to the catheter 310, as it is not necessary to release the collapsible frame 610 from the catheter 310. The catheter 310 enables a surgeon to maintain control over the function and location of the temporary valve 305. Moreover, the catheter 310 can cause the collapsible frame 610 and leaflets 605 to collapse under direct control of the surgeon. For example, and not limitation, if the anchoring conduit is to be positioned in the native aortic valve, the temporary valve 305 can be endovascularly delivered via catheter 310 to a position proximate the native aortic valve in the aorta. Thus, the temporary valve 305 can be expanded and deployed to replace the function of the native aortic valve before the anchoring conduit renders the native aortic valve nonfunctional.

Figure 7:
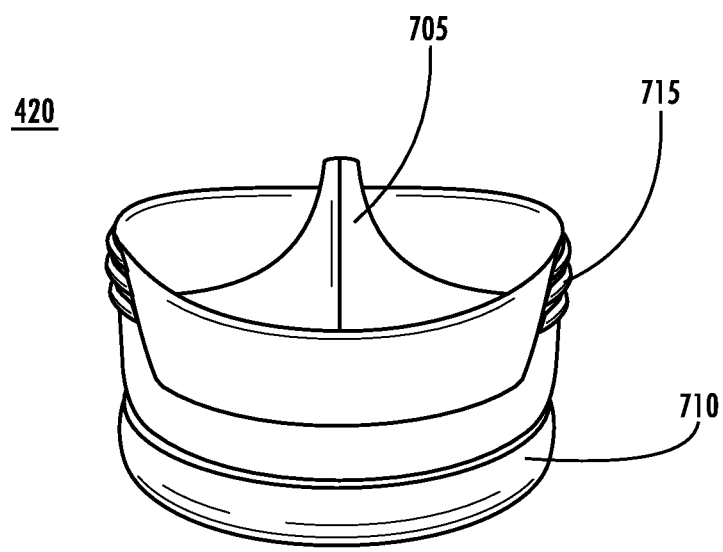
FIG. 7 provides an illustration of an exemplary embodiment of a heart valve prosthesis 420 in accordance with an exemplary embodiment of the present invention.

FIG. 7 provides an illustration of an exemplary embodiment of a heart valve prosthesis 420 in accordance with an exemplary embodiment of the present invention. The heart valve prosthesis 420 in its preferred embodiment is a bioprosthetic valve. The heart valve prosthesis 420 includes a single or plurality of leaflets 705. In an exemplary embodiment, the leaflets 705 may be constructed of treated tissue, such as but not limited to, bovine pericardium or aortic leaflet material. In other embodiments the leaflets 705 may be constructed of a biocompatible polymer.

As shown in FIG. 7, the heart valve prosthesis 420 can have an annulus 710. The annulus 710 may be constructed of biocompatible metals or polymers. Additionally, as shown in FIG. 7, the heart valve prosthesis 420 has a releasably engaging component 715. The releasably engaging component 715 is enabled to be coupled to the releasably engaging component of harbor 415. Thereby, the releasably engaging component 715 of the heart valve prosthesis 420 can be securely attached to the harbor 415. In an exemplary embodiment shown in FIG. 7, the releasably engaging component 715 of the heart valve prosthesis 420 is threading, which can be provided on the side of the heart valve prosthesis 420. The threading of the releasably engaging component 715 can couple to counter-threading of the releasably engaging component 515 (FIG. 5A) of the anchoring conduit 200. Those of skill in the art will appreciate that the releasably engaging component 715 may be many other suitable components including, but not limited to, a screw, magnetic, clamps or latching systems which can releasably engage the heart valve prosthesis 420 with the harbor 415.

The heart valve prosthesis 420 can also be enabled to connected to a catheter or long arm which may be used to deliver the arm to a specific location. In its preferred embodiments the catheter or long arm device which releasably attaches a heart valve prosthesis 420 into the harbor 415, may be constructed of a biocompatible polymer or metal. The long arm device has distal and proximal ends. In the distal end, the catheter or long arm device has a locking component which may releasably hold a heart valve prosthesis 420. This locking component may be a screw, clamp, latching system, or many other suitable components. On the proximal end, the long arm device or catheter contains a control component which can allow the release or coupling of a heart valve. Additionally the long arm device or catheter is controllably flexible in other to direct the heart valve prosthesis 420 to the desired location.

Figure 8:
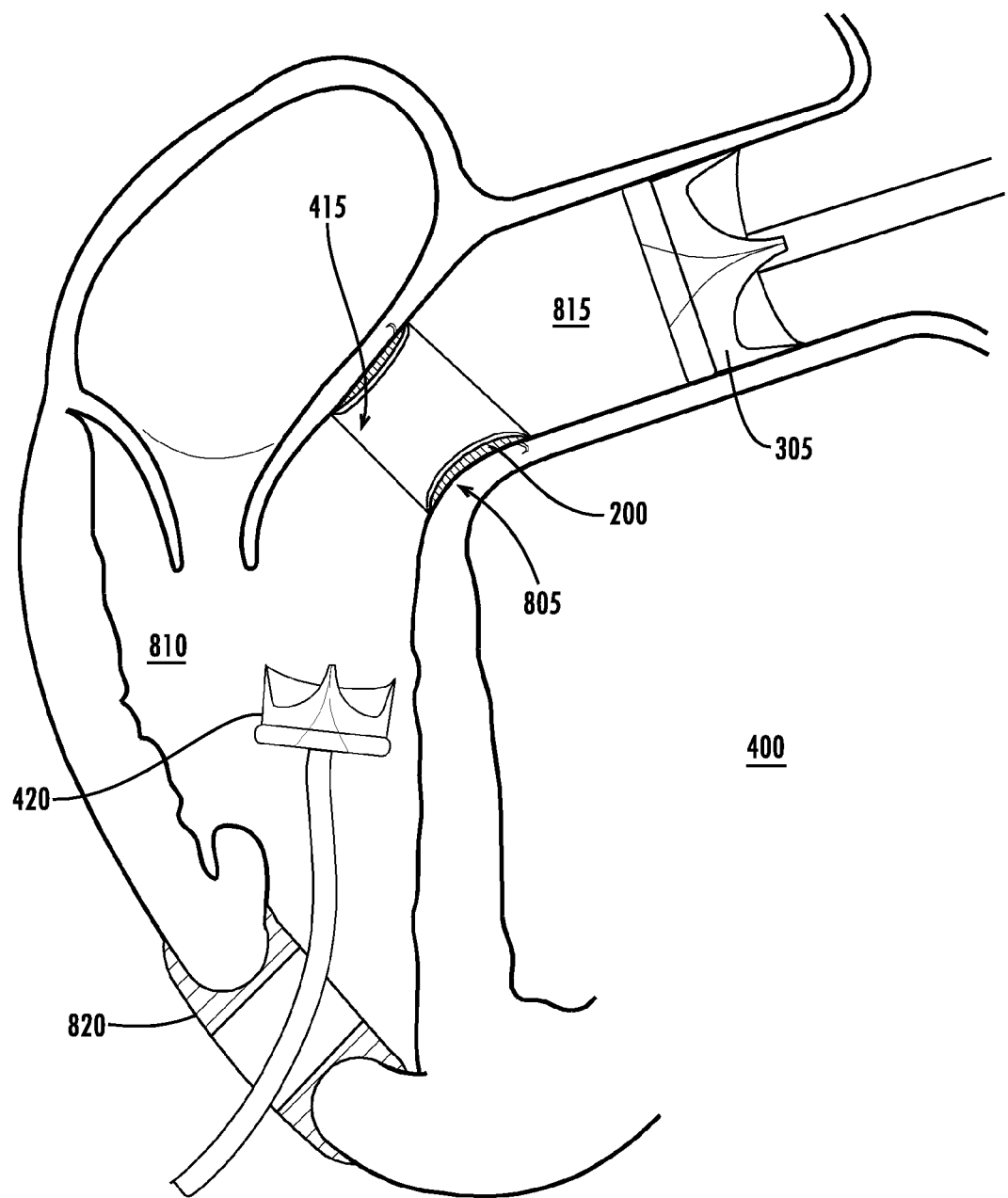
FIG. 8 provides an illustration of an exemplary embodiment of a cardiac prosthetic system 400 implemented in a pulmonic valve in accordance with an exemplary embodiment of the present invention.

FIG. 8 provides an illustration of an exemplary embodiment of a cardiac prosthetic system 400 implemented in a pulmonic valve in accordance with an exemplary embodiment of the present invention. As shown in FIG. 8, the anchoring conduit 200 can be deployed in the pulmonary artery 815 proximate the pulmonic valve 805. In an exemplary embodiment, the anchoring conduit 200 covers the inlet area between the right ventricle 810 and the pulmonary artery 815. In one embodiment, the anchoring conduit 200 can be implemented in an area immediately proximate the pulmonic valve 805. In alternate embodiment, the anchoring conduit 200 can be implemented over a larger portion of the pulmonary artery 815. Those of skill in the art will appreciate that the dimensions and placement location of the anchoring conduit 200 can be modified in a variety of embodiments without detracting from the scope of the invention.

In an exemplary embodiment, the anchoring conduit 200 provides a harbor 415. The harbor 415 can include a releasably engaging component, which is enabled to serve as a receiving port for a heart valve prosthesis 420. The implementation of the anchoring conduit 200 renders the native pulmonic valve 805 non-functional, therefore, an exemplary embodiment of the present invention provides a temporary valve 305 that can be placed in the pulmonary artery 815 to perform the function of the native pulmonic valve 805.

When both the anchoring conduit 200 and the temporary valve 305 are in place, the heart valve prosthesis 420 can be introduced into the heart. In an exemplary embodiment, the heart valve prosthesis 420 is introduced through a port 820 in the heart chamber. The port 820 in the exemplary embodiment depicted in FIG. 8 is mounted on the lower wall of the right ventricle 810 and provides an orifice through which the heart valve prosthesis 420 can be delivered. In the exemplary embodiment depicted in FIG. 8, once the heart valve prosthesis 420 has been introduced into the right ventricle 810, it can be delivered to a harbor 415 on the anchoring conduit 200.

In an exemplary embodiment, the heart valve prosthesis 420 can provide a releasably engaging component enabled to couple to a mating releasably engaging component provided on harbor 415. Once the heart valve prosthesis 420 has been mated to the releasably engaging component of the harbor 415 of the anchoring conduit 200, the harbor 415 can releasably retain the heart valve prosthesis 420, and the heart valve prosthesis 420 can be released from the catheter or long arm.

After heart valve prosthesis 420 is in place, the temporary valve 305 can be extracted. Furthermore, the ports in the venous/arterial system or ports in the heart can be closed in an manner that can allow them to be opened if the heart valve needs to be replaced. Thereby, should the first heart valve prosthesis deployed become deficient, a second heart valve prosthesis can be replaced for the first.

While the invention has been disclosed in its preferred forms, it will be apparent to those skilled in the art that many modifications, additions, and deletions can be made therein without departing from the spirit and scope of the invention and its equivalents as set forth in the following claims.

What is claimed is:

1. A method of preparing a heart valve for replacement comprising:
   delivering an anchoring conduit to a heart valve, the anchoring conduit comprising an expandable structure having an outer layer and an inner layer, the outer layer configured to bend to conform to the contour of a tissue component and the inner layer comprising a smooth and substantially uniform inner surface;
   wherein the expansion of the expandable structure enables the expandable structure to interface with the tissue component and define an open cavity, the open cavity defined at least in part by the inner layer having the smooth and substantially uniform inner surface;
   wherein the anchoring conduit includes a harbor enabled to releasably connect a heart valve prosthesis; and
   expanding the anchoring conduit in the heart valve.

2. The method of preparing a heart valve for replacement of claim 1 further comprising:
   delivering a temporary valve, in a condensed state, to a target site proximate the heart valve; and
   deploying the temporary valve at the target site proximate the heart valve; and
   wherein the temporary valve operates to temporarily replace the function of the heart valve when the anchoring conduit is expanded.

3. The method of preparing a heart valve for replacement of claim 1, wherein the open cavity of the anchoring conduit provides an inner lumen surface against which a heart valve prosthesis can be deployed.

4. The method of preparing a heart valve for replacement of claim 1, wherein the inner surface of the open cavity includes a biocompatible lumen.

5. An anchoring conduit comprising:
   an expandable structure having an outer layer and an inner layer, the outer layer configured to bend to conform to the contour of a tissue component and the inner layer comprising a smooth and substantially uniform inner surface;

wherein the expansion of the expandable structure enables the expandable structure to interface with the tissue component and define an open cavity, the open cavity defined at least in part by the inner layer having the smooth and substantially uniform inner surface; and wherein the anchoring conduit, further comprises a harbor in communication with the expandable structure, the harbor including a first releasably engaging component.

6. The anchoring conduit of claim 5, wherein the anchoring conduit further comprises an anchoring component configured to disable a heart valve.

7. The anchoring conduit of claim 5, wherein the anchoring conduit further comprises an anchoring component configured to disable a native heart valve by compressing the components of the native heart valve against the native heart valve.

8. The anchoring conduit of claim 5, wherein an anchoring component is configured to receive a heart valve prosthesis.

9. The anchoring conduit of claim 8, wherein the expandable structure is configured to enable tissue growth onto the heart valve prosthesis.

10. The anchoring conduit of claim 5, wherein an anchoring component is enabled to be endovascularly delivered.

11. The anchoring conduit of claim 5, wherein a heart valve prosthesis having a second releasably engaging component is enabled to be securely coupled and uncoupled from the first releasably engaging component of the harbor.

12. The anchoring conduit of claim 11, wherein the heart valve prosthesis can be coupled and uncoupled from the first releasably engaging component of the harbor within the heart.

13. The anchoring conduit of claim 5, wherein the expandable structure is configured to contain a plurality of debris released from the tissue component.

14. The anchoring conduit of claim 5, wherein the expandable structure is configured to expand and adapt to the geometry of the sinuses of the valsalva.

15. The anchoring conduit of claim 5, wherein the anchoring conduit can be delivered through the apex of a heart.

16. The anchoring conduit of claim 5, wherein the expandable structure comprises a proximal anchor component and a distal anchor component.

17. The anchoring component of claim 16, wherein the proximal anchor component and the distal anchor component are configured to interface with the tissue component.

18. A method of improving a valve competency comprising:
   providing the anchoring conduit of claim 5 to an area proximate a heart valve, wherein the harbor is enabled to releasably connect a heart valve prosthesis;
   deploying the anchoring conduit, the deployment of the anchoring conduit defining the open cavity; and
   deploying a heart valve prosthesis in the open cavity of the anchoring conduit.

19. The method of improving a valve competency of claim 18, wherein deploying the heart valve prosthesis involves expanding the heart valve prosthesis within the open cavity of the anchoring conduit.

20. The method of improving a valve competency of claim 18, wherein the anchoring conduit provides a first releasably engaging component and the heart valve prosthesis provides a second releasably engaging component enabled to be securely coupled and uncoupled from the first releasably engaging component of the anchoring conduit.

21. The method of improving a valve competency of claim 20, wherein deploying the heart valve prosthesis involves securely coupling the second releasably engaging component of the heart valve prosthesis to the first releasably engaging component of the anchoring conduit.

22. The method of improving a valve competency of claim 21, further comprising:
   removing the heart valve prosthesis from the anchoring conduit; and
   deploying a second heart valve prosthesis in the open cavity of the anchoring conduit.

23. A method of improving a deficient heart valve comprising:
   delivering the anchoring conduit of claim 5 to a heart valve;
   delivering a temporary valve, in a condensed state, to a target site proximate the heart valve;
   deploying the temporary valve at the target site proximate the heart valve; and
   deploying the anchoring conduit in the heart valve, the deployment of the anchoring conduit disabling the heart valve; and
   wherein the temporary valve operates to temporarily replace the function of the heart valve when the anchoring conduit is expanded.

24. The method of improving a deficient heart valve of claim 23, further comprising:
   delivering the heart valve prosthesis to an area in the heart proximate the anchoring conduit; and
   coupling the heart valve prosthesis to the harbor of the anchoring conduit.

25. The method of improving a deficient heart valve of claim 24, further comprising removing the temporary valve.

26. The method of improving a deficient heart valve of claim 25, further comprising:
   delivering a temporary valve, in a condensed state, to a target site in an artery proximate the heart valve;
   expanding the temporary valve at the target site in the artery proximate the heart valve;
   decoupling the heart valve prosthesis from the harbor of the anchoring conduit;
   delivering a second heart valve prosthesis to an area in the heart proximate the anchoring conduit; and
   coupling the second heart valve prosthesis to the harbor of the anchoring conduit.

27. The method of improving a deficient heart valve of claim 26, further comprising removing the temporary valve.

28. The method of improving a deficient heart valve of claim 24, wherein the temporary valve and the heart valve prosthesis are endovascularly delivered.

29. The method of improving a deficient heart valve of claim 28, wherein the heart valve prosthesis can be delivered through a conduit in the temporary valve.

30. The method of improving a deficient heart valve of claim 23, wherein the heart valve is an aortic valve.

31. The method of improving a deficient heart valve of claim 23, wherein the heart valve is a pulmonic valve.

32. A cardiac prosthetic system comprising:
   the anchoring conduit of claim 5; a temporary valve; and
   a heart valve prosthesis having a second releasably engaging component enabled to be securely coupled and uncoupled from the first releasably engaging component of the harbor.

33. The cardiac prosthetic system of claim 32, further comprising a second heart valve prosthesis, the second heart valve prosthesis having a third releasably engaging component enabled to be coupled and uncoupled from the first releasably engaging component of the harbor.

34. The cardiac prosthetic system of claim 32, wherein the anchoring conduit is enabled to be deployed in an aortic heart valve.

35. The cardiac prosthetic system of claim 32, wherein the anchoring conduit is enabled to be deployed in a pulmonic heart valve.

36. The cardiac prosthetic system of claim 32, wherein the anchoring conduit is enabled to be delivered through a blood vessel.

37. The cardiac prosthetic system of claim 32, wherein the temporary valve is enabled to temporarily perform the function of a heart valve.

38. The cardiac prosthetic system of claim 32, wherein the temporary valve and the heart valve prosthesis are endovascularly delivered.

39. The cardiac prosthetic system of claim 38, wherein the heart valve prosthesis can be delivered through a conduit in the temporary valve.

40. A cardiac device comprising:
   a heart valve prosthesis having a releasably engaging component; and
   the anchoring conduit of claim 5; wherein the releasably engaging component is enabled to be connected to the harbor located within a heart.

41. The cardiac device of claim 40, wherein the releasably engaging component of the harbor is capable of being coupled to the releasably engaging component of the heart valve prosthesis.

42. The cardiac device of claim 40, wherein the heart valve prosthesis is enabled to be released from its connection to the harbor located within the heart.

* * * * *